(12) United States Patent
Imaizumi et al.

(10) Patent No.: US 9,695,235 B2
(45) Date of Patent: Jul. 4, 2017

(54) METHOD FOR REGULATING CELL PROLIFERATION

(71) Applicant: Hiroshima University, Higashihiroshima-shi, Hiroshima (JP)

(72) Inventors: Kazunori Imaizumi, Hiroshima (JP); Atsushi Saito, Hiroshima (JP)

(73) Assignee: Hiroshima University, Hiroshima (JP)

( * ) Notice: Subject to any disclaimer, the term of this patent is extended or adjusted under 35 U.S.C. 154(b) by 0 days.

(21) Appl. No.: 14/424,864

(22) PCT Filed: Aug. 28, 2013

(86) PCT No.: PCT/JP2013/072964
§ 371 (c)(1),
(2) Date: Feb. 27, 2015

(87) PCT Pub. No.: WO2014/034700
PCT Pub. Date: Mar. 6, 2014

(65) Prior Publication Data
US 2015/0225469 A1 Aug. 13, 2015

(30) Foreign Application Priority Data
Aug. 30, 2012 (JP) ................................ 2012-189369

(51) Int. Cl.
| | |
|---|---|
| *C07K 16/28* | (2006.01) |
| *C07K 14/47* | (2006.01) |
| *C07K 16/18* | (2006.01) |
| *G01N 33/50* | (2006.01) |
| *A61K 31/713* | (2006.01) |
| *A61K 38/17* | (2006.01) |
| *C12N 15/115* | (2010.01) |

(52) U.S. Cl.
CPC ............ *C07K 16/28* (2013.01); *A61K 31/713* (2013.01); *A61K 38/177* (2013.01); *A61K 38/1709* (2013.01); *C07K 14/4705* (2013.01); *C07K 16/18* (2013.01); *C12N 15/115* (2013.01); *G01N 33/5011* (2013.01); *C07K 2317/73* (2013.01); *C07K 2317/76* (2013.01); *C12N 2310/14* (2013.01); *C12N 2320/30* (2013.01)

(58) Field of Classification Search
CPC ............ C07K 14/4705; G01N 33/5011; A61K 38/177; A61K 38/1709
USPC .......................................... 435/7.1; 514/19.3
See application file for complete search history.

(56) References Cited

FOREIGN PATENT DOCUMENTS

| | | |
|---|---|---|
| JP | 2009-131169 A | 6/2009 |
| KR | 10-2008-0042349 A | 5/2008 |
| WO | 2007/059157 A1 | 5/2007 |

OTHER PUBLICATIONS

Vile et al (Gene Therapy, vol. 7, pp. 2-8, 2000).*
Rochlitz C. F. (Swiss Medicine Weekly, 131:4-9, 2001).*
Glick (Gen. Engineer. News 28(7) pp. 6 and 9 (Apr. 1, 2008)).*
Saito et al. Molecular Cell 53:127-139 (2014).*
Iwamoto et al. PLOS One 10(5): 1-17 (May 8, 2015).*
Imaizumi Clin. Calcium 25(1):29-36 (2015); abstract only).*
Kondo et al., "BBF2H7, a Novel Transmembrane bZIP Transcription Factor, Is a New Type of Endoplasmic Reticulum Stress Transducer," Molecular and Cellular Biology, 27: 1716-1729 (2007).
Saito et al., "Regulation of endoplasmic reticulum stress response by a BBF2H7-mediated Sec23a pathway is essential for chondrogenesis," Nature Cell Biology, 11: 1197-1204 (2009).
Sakai et al., "Molecular Identification of the Sterol-Regulated Luminal Protease that Cleaves SREBPs and Controls Lipid Composition of Animal Cells," Molecular Cell, 2: 505-514 (1998).
Izumi et al., Journal of the Japanese Orthopaedic Association, 86: S1245 (2012).
Izumi et al., Annual Meeting of the Japanese Society for Bone and Mineral Research: Program & Abstracts, 30: 209 (2012).
Kanemoto et al., Annual Meeting of the Japanese Society for Bone and Mineral Research: Program & Abstracts, 29: 217 (2011).
Ishikura-Kinoshita et al., "BBF2H7-Mediated Sec23A Pathway Is Required for Endoplasmic Reticulum-to-Golgi Trafficking in Dermal Fibroblasts to Promote Collagen Synthesis," Journal of Investigative Dermatology, 132: 2010-2018 (2012).
International Search Report issued in corresponding International Patent Application No. PCT/JP2013/072964 dated Oct. 8, 2013.
International Preliminary Report on Patentability and Written Opinion issued in corresponding International Patent Application No. PCT/JP2013/072964 dated Mar. 3, 2015.
Extended European Search Report issued in corresponding European Patent Application No. 13833878.5 dated Mar. 18, 2016.
Storlazzi et al., "Fusion of the FUS and BBF2H7 genes in low grade fibromyxoid sarcoma," Human Molecular Genetics, 12: 2349-2358 (2003).

* cited by examiner

*Primary Examiner* — Lynn Bristol
(74) *Attorney, Agent, or Firm* — Morgan, Lewis & Bockius LLP

(57) ABSTRACT

The present invention provides a composition for regulating cell proliferation comprising a peptide having a partial amino acid sequence of BBF2H7 or an antibody capable of binding to the peptide. The problem has been solved by preparation of the peptide having a partial amino acid sequence of BBF2H7 which has a cell proliferation activity.

20 Claims, 10 Drawing Sheets

Fig.7
A

| | | | |
|---|---|---|---|
| Human BBF2H7 | 1 | MEVLESGEQGVLGMDRKLSELSEPGDGEALMYNTHFSELLDEFSQMVLGQLLNDPFLSEK | 60 |
| Mouse BBF2H7 | 1 | MEVLESGEQSVLGMDRKLSELSEPGETEALMYHTHFSELLDEFSQMVLGQLLSDPFLSEK | 60 |
| Human BBF2H7 | 61 | SVSMEVEPSPTSPAPLIQAEHSYSLGEEPRAQSPFTHTTTSDSFMDDEVESEKMYLSTDF | 120 |
| Mouse BBF2H7 | 61 | SESMEVEPSPTSPAPLIQAEHSYSLSEEPRTQSPFTHAATSDSFMDEFVESEKMYLSTEF | 120 |
| Human BBF2H7 | 121 | PSTSIKTEPVTDEPPPGLVPSVTLTITAISTPLEKEEPPLEMMTGVDSSCQTIIPKIKLE | 180 |
| Mouse BBF2H7 | 121 | PSATIKTEPITEEQPPGLVPSVTLTITAISTPFEKEESPLDMMAGGDSSCQTLIPKIKLE | 180 |
| Human BBF2H7 | 181 | PMEVDQFLMFSPKEAPVDMLHLPPTPPSSHGSDSEGSLSPMPRLHPFSLPQTHSPSRAAP | 240 |
| Mouse BBF2H7 | 181 | PMEVDQFLMFSPKEASVDQLHLPPTPPSSHSSDSEGSLSPMPRLHPFSLSQAHSPARAMP | 240 |
| Human BBF2H7 | 241 | RAPSALSSSPLLTAPHKQQGSGPLVLTEEEKRTLIAEGYPIPTKLPLSKSEEKALKKIRR | 300 |
| Mouse BBF2H7 | 241 | RGPSALSTSPLLTAPHKQQGSGPLVLTEEEKRTLVAEGYPIPTKLPLTKSEEKALKKIRR | 300 |
| Human BBF2H7 | 301 | KIKNKISAQESRRKKKEYMDSLEKKVESCSTEMLELRKKVEVLENTNRTLLQQLQKLQTL | 360 |
| Mouse BBF2H7 | 301 | KIKNKISAQESRRKKKEYMDSLEKKVESCSTEMLELRKKVEVLENTNRTLLQQLQKLQTL | 360 |
| Human BBF2H7 | 361 | VMGKVSRTCKLAGTQTGTCLMVVVLCFAVAFGSFFQGYGPYPSATKMALPSGHSLQEPYT | 420 |
| Mouse BBF2H7 | 361 | VMGKVSRTCKLAGTQTGTCLMVVVLCFAVAFGSFFQGYGPYPSATKMALPSQHPLSEPYT | 420 |
| Human BBF2H7 | 421 | ASVVRSRNLL | 430 (Base 1-140 of SEQ ID NO: 3) |
| Mouse BBF2H7 | 421 | ASVVRSRNLL | 430 (Base 1-140 of SEQ ID NO: 4) |

B

| | | | |
|---|---|---|---|
| Human BBF2H7 | 431 | IYEEHSPPEESSSPGSAGELGGMDRGSSLLRYS-GLESRPDVDLPHFIISNETSLEKSVL | 489 |
| Mouse BBF2H7 | 431 | IYEEHAPLEESSSPASAGELGGMDRGSSLLRASSGLEALPEVDLPHFLISNETSLERSVL | 490 |
| Human BBF2H7 | 490 | LELQQHLVSAKLEGNETLKVVELDRRVNTTF | 520 (Base 431-520 of SEQ ID NO: 3) |
| Mouse BBF2H7 | 491 | LELQQHLVSSKLEGNETLKVVELERRVNATF | 521 (Base 431-521 of SEQ ID NO: 4) |

Fig.8

BBF2H7 Full length-Luc.    | Full length BBF2H7 | Luc. |
                           1                    521

BBF2H7 N-terminus-Luc.     | BBF2H7 N-terminus | Luc. |
                           1                   377

BBF2H7 C-terminus-Luc.     | BBF2H7 C-terminus | Luc. |
                           431                 521

SEQUENCE LISTING

```
<160> NUMBER OF SEQ ID NOS: 22

<210> SEQ ID NO 1
<211> LENGTH: 90
<212> TYPE: PRT
<213> ORGANISM: human

<400> SEQUENCE: 1

Ile Tyr Glu Glu His Ser Pro Pro Glu Glu Ser Ser Ser Pro Gly Ser
1               5                   10                  15

Ala Gly Glu Leu Gly Gly Trp Asp Arg Gly Ser Ser Leu Leu Arg Val
            20                  25                  30

Ser Gly Leu Glu Ser Arg Pro Asp Val Asp Leu Pro His Phe Ile Ile
        35                  40                  45

Ser Asn Glu Thr Ser Leu Glu Lys Ser Val Leu Leu Glu Leu Gln Gln
    50                  55                  60

His Leu Val Ser Ala Lys Leu Glu Gly Asn Glu Thr Leu Lys Val Val
```

```
            65                  70                  75                  80

Glu Leu Asp Arg Arg Val Asn Thr Thr Phe
                85                  90

<210> SEQ ID NO 2
<211> LENGTH: 91
<212> TYPE: PRT
<213> ORGANISM: mouse

<400> SEQUENCE: 2

Ile Tyr Glu Glu His Ala Pro Leu Glu Glu Ser Ser Pro Ala Ser
1               5                   10                  15

Ala Gly Glu Leu Gly Gly Trp Asp Arg Gly Ser Ser Leu Leu Arg Ala
                20                  25                  30

Ser Ser Gly Leu Glu Ala Leu Pro Glu Val Asp Leu Pro His Phe Leu
            35                  40                  45

Ile Ser Asn Glu Thr Ser Leu Glu Lys Ser Val Leu Leu Glu Leu Gln
        50                  55                  60

Gln His Leu Val Ser Ser Lys Leu Glu Gly Asn Glu Thr Leu Lys Val
65                  70                  75                  80

Val Glu Leu Glu Arg Arg Val Asn Ala Thr Phe
                85                  90

<210> SEQ ID NO 3
<211> LENGTH: 520
<212> TYPE: PRT
<213> ORGANISM: human

<400> SEQUENCE: 3

Met Glu Val Leu Glu Ser Gly Glu Gln Gly Val Leu Gln Trp Asp Arg
1               5                   10                  15

Lys Leu Ser Glu Leu Ser Glu Pro Gly Asp Gly Glu Ala Leu Met Tyr
                20                  25                  30

His Thr His Phe Ser Glu Leu Leu Asp Glu Phe Ser Gln Asn Val Leu
            35                  40                  45

Gly Gln Leu Leu Asn Asp Pro Phe Leu Ser Glu Lys Ser Val Ser Met
        50                  55                  60

Glu Val Glu Pro Ser Pro Thr Ser Pro Ala Pro Leu Ile Gln Ala Glu
65                  70                  75                  80

His Ser Tyr Ser Leu Cys Glu Glu Pro Arg Ala Gln Ser Pro Phe Thr
                85                  90                  95

His Ile Thr Thr Ser Asp Ser Phe Asn Asp Asp Glu Val Glu Ser Glu
            100                 105                 110

Lys Trp Tyr Leu Ser Thr Asp Phe Pro Ser Thr Ser Ile Lys Thr Glu
        115                 120                 125

Pro Val Thr Asp Glu Pro Pro Gly Leu Val Pro Ser Val Thr Leu
130                 135                 140

Thr Ile Thr Ala Ile Ser Thr Pro Leu Glu Lys Glu Pro Pro Leu
145                 150                 155                 160

Glu Met Asn Thr Gly Val Asp Ser Ser Cys Gln Thr Ile Ile Pro Lys
                165                 170                 175

Ile Lys Leu Glu Pro His Glu Val Asp Gln Phe Leu Asn Phe Ser Pro
            180                 185                 190

Lys Glu Ala Pro Val Asp His Leu His Leu Pro Pro Thr Pro Pro Ser
        195                 200                 205

Ser His Gly Ser Asp Ser Glu Gly Ser Leu Ser Pro Asn Pro Arg Leu
```

His Pro Phe Ser Leu Pro Gln Thr His Ser Pro Ser Arg Ala Ala Pro
225                 230                 235                 240

Arg Ala Pro Ser Ala Leu Ser Ser Pro Leu Leu Thr Ala Pro His
            245                 250                 255

Lys Leu Gln Gly Ser Gly Pro Leu Val Leu Thr Glu Glu Lys Arg
            260                 265                 270

Thr Leu Ile Ala Glu Gly Tyr Pro Ile Pro Thr Lys Leu Pro Leu Ser
            275                 280                 285

Lys Ser Glu Glu Lys Ala Leu Lys Lys Ile Arg Arg Lys Ile Lys Asn
290                 295                 300

Lys Ile Ser Ala Gln Glu Ser Arg Arg Lys Lys Lys Glu Tyr Met Asp
305                 310                 315                 320

Ser Leu Glu Lys Lys Val Glu Ser Cys Ser Thr Glu Asn Leu Glu Leu
            325                 330                 335

Arg Lys Lys Val Glu Val Leu Glu Asn Thr Asn Arg Thr Leu Leu Gln
            340                 345                 350

Gln Leu Gln Lys Leu Gln Thr Leu Val Met Gly Lys Val Ser Arg Thr
            355                 360                 365

Cys Lys Leu Ala Gly Thr Gln Thr Gly Thr Cys Leu Met Val Val Val
370                 375                 380

Leu Cys Phe Ala Val Ala Phe Gly Ser Phe Phe Gln Gly Tyr Gly Pro
385                 390                 395                 400

Tyr Pro Ser Ala Thr Lys Met Ala Leu Pro Ser Gln His Ser Leu Gln
            405                 410                 415

Glu Pro Tyr Thr Ala Ser Val Val Arg Ser Arg Asn Leu Leu Ile Tyr
            420                 425                 430

Glu Glu His Ser Pro Pro Glu Ser Ser Ser Pro Gly Ser Ala Gly
            435                 440                 445

Glu Leu Gly Gly Trp Asp Arg Gly Ser Ser Leu Leu Arg Val Ser Gly
            450                 455                 460

Leu Glu Ser Arg Pro Asp Val Asp Leu Pro His Phe Ile Ile Ser Asn
465                 470                 475                 480

Glu Thr Ser Leu Glu Lys Ser Val Leu Leu Glu Leu Gln Gln His Leu
            485                 490                 495

Val Ser Ala Lys Leu Glu Gly Asn Glu Thr Leu Lys Val Val Glu Leu
            500                 505                 510

Asp Arg Arg Val Asn Thr Thr Phe
            515                 520

<210> SEQ ID NO 4
<211> LENGTH: 521
<212> TYPE: PRT
<213> ORGANISM: mouse

<400> SEQUENCE: 4

Met Glu Val Leu Glu Ser Gly Glu Gln Ser Val Leu Gln Trp Asp Arg
1               5                   10                  15

Lys Leu Ser Glu Leu Ser Glu Pro Gly Glu Thr Glu Ala Leu Met Tyr
            20                  25                  30

His Thr His Phe Ser Glu Leu Leu Asp Glu Phe Ser Gln Asn Val Leu
        35                  40                  45

Gly Gln Leu Leu Ser Asp Pro Phe Leu Ser Glu Lys Ser Glu Ser Met
    50                  55                  60

-continued

```
Glu Val Glu Pro Ser Pro Thr Ser Pro Ala Pro Leu Ile Gln Ala Glu
65              70                  75                  80

His Ser Tyr Ser Leu Ser Glu Glu Pro Arg Thr Gln Ser Pro Phe Thr
                85                  90                  95

His Ala Ala Thr Ser Asp Ser Phe Asn Asp Glu Glu Val Glu Ser Glu
            100                 105                 110

Lys Trp Tyr Leu Ser Thr Glu Phe Pro Ser Ala Thr Ile Lys Thr Glu
            115                 120                 125

Pro Ile Thr Glu Glu Gln Pro Pro Gly Leu Val Pro Ser Val Thr Leu
        130                 135                 140

Thr Ile Thr Ala Ile Ser Thr Pro Phe Glu Lys Glu Ser Pro Leu
145                 150                 155                 160

Asp Met Asn Ala Gly Gly Asp Ser Ser Cys Gln Thr Leu Ile Pro Lys
                165                 170                 175

Ile Lys Leu Glu Pro His Glu Val Asp Gln Phe Leu Asn Phe Ser Pro
            180                 185                 190

Lys Glu Ala Ser Val Asp Gln Leu His Leu Pro Pro Thr Pro Pro Ser
        195                 200                 205

Ser His Ser Ser Asp Ser Glu Gly Ser Leu Ser Pro Asn Pro Arg Leu
    210                 215                 220

His Pro Phe Ser Leu Ser Gln Ala His Ser Pro Ala Arg Ala Met Pro
225                 230                 235                 240

Arg Gly Pro Ser Ala Leu Ser Thr Ser Pro Leu Leu Thr Ala Pro His
                245                 250                 255

Lys Leu Gln Gly Ser Gly Pro Leu Val Leu Thr Glu Glu Lys Arg
            260                 265                 270

Thr Leu Val Ala Glu Gly Tyr Pro Ile Pro Thr Lys Leu Pro Leu Thr
        275                 280                 285

Lys Ser Glu Glu Lys Ala Leu Lys Lys Ile Arg Arg Lys Ile Lys Asn
    290                 295                 300

Lys Ile Ser Ala Gln Glu Ser Arg Arg Lys Lys Glu Tyr Met Asp
305                 310                 315                 320

Ser Leu Glu Lys Lys Val Glu Ser Cys Ser Thr Glu Asn Leu Glu Leu
                325                 330                 335

Arg Lys Lys Val Glu Val Leu Glu Asn Thr Asn Arg Thr Leu Leu Gln
            340                 345                 350

Gln Leu Gln Lys Leu Gln Thr Leu Val Met Gly Lys Val Ser Arg Thr
        355                 360                 365

Cys Lys Leu Ala Gly Thr Gln Thr Gly Thr Cys Leu Met Val Val Val
    370                 375                 380

Leu Cys Phe Ala Val Ala Phe Gly Ser Phe Phe Gln Gly Tyr Gly Pro
385                 390                 395                 400

Tyr Pro Ser Ala Thr Lys Met Ala Leu Pro Ser Gln His Pro Leu Ser
                405                 410                 415

Glu Pro Tyr Thr Ala Ser Val Val Arg Ser Arg Asn Leu Leu Ile Tyr
            420                 425                 430

Glu Glu His Ala Pro Leu Glu Glu Ser Ser Pro Ala Ser Ala Gly
        435                 440                 445

Glu Leu Gly Gly Trp Asp Arg Gly Ser Ser Leu Leu Arg Ala Ser Ser
    450                 455                 460

Gly Leu Glu Ala Leu Pro Glu Val Asp Leu Pro His Phe Leu Ile Ser
465                 470                 475                 480

Asn Glu Thr Ser Leu Glu Lys Ser Val Leu Leu Glu Leu Gln Gln His
```

```
                    485                 490                 495
Leu Val Ser Ser Lys Leu Glu Gly Asn Glu Thr Leu Lys Val Val Glu
            500                 505                 510

Leu Glu Arg Arg Val Asn Ala Thr Phe
            515                 520

<210> SEQ ID NO 5
<211> LENGTH: 30
<212> TYPE: DNA
<213> ORGANISM: Artificial
<220> FEATURE:
<223> OTHER INFORMATION: PCR primer

<400> SEQUENCE: 5
gcggccgctt cgacactttg tctgccactc                                        30

<210> SEQ ID NO 6
<211> LENGTH: 32
<212> TYPE: DNA
<213> ORGANISM: Artificial
<220> FEATURE:
<223> OTHER INFORMATION: PCR primer

<400> SEQUENCE: 6
ctcgagtcac tccgagaagt gctgcaagaa gc                                     32

<210> SEQ ID NO 7
<211> LENGTH: 23
<212> TYPE: DNA
<213> ORGANISM: Artificial
<220> FEATURE:
<223> OTHER INFORMATION: PCR primer

<400> SEQUENCE: 7
cagagatgcc ctgagatcag ctg                                               23

<210> SEQ ID NO 8
<211> LENGTH: 30
<212> TYPE: DNA
<213> ORGANISM: Artificial
<220> FEATURE:
<223> OTHER INFORMATION: PCR primer

<400> SEQUENCE: 8
ggtaccctac accatgcgcc accagccatg                                        30

<210> SEQ ID NO 9
<211> LENGTH: 21
<212> TYPE: DNA
<213> ORGANISM: Artificial
<220> FEATURE:
<223> OTHER INFORMATION: PCR primer

<400> SEQUENCE: 9
ctgcagtggt cagatggaca g                                                 21

<210> SEQ ID NO 10
<211> LENGTH: 26
<212> TYPE: DNA
<213> ORGANISM: Artificial
<220> FEATURE:
<223> OTHER INFORMATION: PCR primer

<400> SEQUENCE: 10
tggctgcgct gctgcccaag acccag                                            26
```

```
<210> SEQ ID NO 11
<211> LENGTH: 20
<212> TYPE: DNA
<213> ORGANISM: Artificial
<220> FEATURE:
<223> OTHER INFORMATION: PCR primer

<400> SEQUENCE: 11
cttgacgagt tcttctgagg                                              20

<210> SEQ ID NO 12
<211> LENGTH: 61
<212> TYPE: PRT
<213> ORGANISM: human

<400> SEQUENCE: 12
```

Ile Tyr Glu Glu His Ser Pro Pro Glu Glu Ser Ser Pro Gly Ser
1               5                   10                  15

Ala Gly Glu Leu Gly Gly Trp Asp Arg Gly Ser Ser Leu Leu Arg Val
            20                  25                  30

Ser Gly Leu Glu Ser Arg Pro Asp Val Asp Leu Pro His Phe Ile Ile
        35                  40                  45

Ser Asn Glu Thr Ser Leu Glu Lys Ser Val Leu Leu Glu
    50                  55                  60

```
<210> SEQ ID NO 13
<211> LENGTH: 19
<212> TYPE: DNA
<213> ORGANISM: Artificial
<220> FEATURE:
<223> OTHER INFORMATION: PCR primer

<400> SEQUENCE: 13
taggccctca gcctcactc                                               19

<210> SEQ ID NO 14
<211> LENGTH: 20
<212> TYPE: DNA
<213> ORGANISM: Artificial
<220> FEATURE:
<223> OTHER INFORMATION: PCR primer

<400> SEQUENCE: 14
ccacccctgg gataaagcac                                              20

<210> SEQ ID NO 15
<211> LENGTH: 19
<212> TYPE: DNA
<213> ORGANISM: Artificial
<220> FEATURE:
<223> OTHER INFORMATION: PCR primer

<400> SEQUENCE: 15
cagagcagcg agcaggagc                                               19

<210> SEQ ID NO 16
<211> LENGTH: 20
<212> TYPE: DNA
<213> ORGANISM: Artificial
<220> FEATURE:
<223> OTHER INFORMATION: PCR primer

<400> SEQUENCE: 16
```

```
gcagctgctt ccacaccact                                                    20

<210> SEQ ID NO 17
<211> LENGTH: 20
<212> TYPE: DNA
<213> ORGANISM: Artificial
<220> FEATURE:
<223> OTHER INFORMATION: PCR primer

<400> SEQUENCE: 17
ctgccattct caccgtgtcc                                                    20

<210> SEQ ID NO 18
<211> LENGTH: 20
<212> TYPE: DNA
<213> ORGANISM: Artificial
<220> FEATURE:
<223> OTHER INFORMATION: PCR primer

<400> SEQUENCE: 18
agcttgatgg acccctctgc                                                    20

<210> SEQ ID NO 19
<211> LENGTH: 20
<212> TYPE: DNA
<213> ORGANISM: Artificial
<220> FEATURE:
<223> OTHER INFORMATION: PCR primer

<400> SEQUENCE: 19
cgagcgtaag atccctgct                                                     20

<210> SEQ ID NO 20
<211> LENGTH: 20
<212> TYPE: DNA
<213> ORGANISM: Artificial
<220> FEATURE:
<223> OTHER INFORMATION: PCR primer

<400> SEQUENCE: 20
gcaccgacac caatttcagc                                                    20

<210> SEQ ID NO 21
<211> LENGTH: 20
<212> TYPE: DNA
<213> ORGANISM: Artificial
<220> FEATURE:
<223> OTHER INFORMATION: PCR primer

<400> SEQUENCE: 21
ggatcggata ggtggtcttc                                                    20

<210> SEQ ID NO 22
<211> LENGTH: 20
<212> TYPE: DNA
<213> ORGANISM: Artificial
<220> FEATURE:
<223> OTHER INFORMATION: PCR primer

<400> SEQUENCE: 22
ccaacttctg gctcttcctg                                                    20
```

METHOD FOR REGULATING CELL PROLIFERATION

A computer readable text file, entitled "SequenceListing.txt," created on or about Feb. 27, 2015 with a file size of about 15 kb contains the sequence listing for this application and is hereby incorporated by reference in its entirety.

TECHNICAL FIELD

The present application claims priority to Japanese patent application no. 2012-189369 filed on Aug. 30, 2012, the content of which is incorporated herein by reference in its entirety.

The present invention relates to use of a peptide having a partial amino acid sequence of BBF2H7 (BBF2 human homologue on chromosome 7), a nucleic acid molecule encoding the amino acid sequence, or an antibody against the BBF2H7 partial peptide for regulating cell proliferation, i.e. for promoting cell proliferation or suppressing cell proliferation.

BACKGROUND ART

Most of proteins are synthesized in the endoplasmic reticulum (ER) in cells and appropriately folded to gain their proper functions. When cells are exposed to an abnormal environment, the function of the ER may be disrupted and a large amount of defective proteins may be produced in the ER. Cells have some proteins which can detect such abnormal situations as above. When the abnormal situation has been detected, the cells can actively repair or degrade the abnormal proteins, thereby protecting themselves from toxicity of the abnormal proteins. BBF2H7 has been reported as a protein involved in this mechanism. (Non-Patent Literature 1).

Involvement of BBF2H7 in cartilage formation has been suggested. It has been reported that in chondrocytes of BBF2H7-knockout mice cartilage matrix proteins are not secreted extracellularly and accumulate in the ER (Non-Patent Literature 2). It also has been reported that BBF2H7 promotes synthesis of Sec23a, a protein essential for formation of the transport vesicles (Non-Patent Literature 2). Furthermore, it has been reported that BBF2H7 is subjected to regulated intramembrane proteolysis by Site-1 protease (Non-Patent Literature 3).

On the other hand, abnormalities in hedgehog signaling have been reported in various cancers including, for example, basal cell carcinoma, neuroectodermal tumors such as medullablastoma, meningioma, hemangioma, glioblastoma, pancreatic adenocarcinoma, squamous lung carcinoma, small-cell lung carcinoma, non-small cell lung carcinoma, chondrosarcoma, breast cancer, rhabdomyosarcoma, oesophageal cancer, stomach cancer, biliary tract cancer, renal cancer, and thyroid cancer (Patent Literature 1). Actually, vismodegib, an inhibitor of hedgehog signaling, has been approved for treating basal cell carcinoma in countries including the United States.

CITATION LIST

Patent Literature

Patent Literature 1: WO2007/059157

Non-patent Literature

Non-Patent Literature 1: Kondo S, Saito A, Hino S, Murakami T, Ogata M, Kanemoto S, Nara S, Yamashita A, Yoshinaga K, Hara H, Imaizumi K, Mol Cell Biol. 2007 March; 27(5):1716-29 Non-Patent Literature 2: Saito A, Hino S, Murakami T, Kanemoto S, Kondo S, Saitoh M, Nishimura R, Yoneda T, Furuichi T, Ikegawa S, Ikawa M, Okabe M, Imaizumi K., Nat Cell Biol. 2009 October; 11(10):1197-204. Epub 2009 Sep. 20 Non-Patent Literature 3: Kondo S, Saito A, Hino S-I, Murakami T, Ogata M, Kanemoto S, Nara S, Yamashita A, Yoshinaga K, Hara H, Imaizumi K., Molecular and Cellular

SUMMARY OF INVENTION

The inventors have found that a BBF2H7 partial peptide produced by regulated intramembrane proteolysis with Site-1 protease and secreted extracellularly plays a role in cell proliferation. The inventors also have found that the BBF2H7 C-terminus peptide regulates hedgehog signaling and achieved the present invention.

In one aspect, the present invention provides a composition for promoting cell proliferation, comprising a substance that potentiates signaling induced by the extracellularly secreted BBF2H7 partial peptide. In one embodiment, the present invention provides a composition for promoting cell proliferation, comprising a peptide consisting of the amino acid sequence represented by SEQ ID NO.: 1 or SEQ ID NO.: 2. In another embodiment, the present invention provides a composition for promoting cell proliferation, comprising a nucleic acid molecule encoding the amino acid sequence represented by SEQ ID NO.: 1 or SEQ ID NO.: 2.

In one aspect, the present invention provides a composition for suppressing cell proliferation, comprising a substance that suppresses signaling induced by the extracellularly secreted BBF2H7 partial peptide. In one embodiment, the present invention provides a composition for suppressing cell proliferation, comprising an antibody or antibody fragment thereof capable of binding to a peptide consisting of the amino acid sequence represented by SEQ ID NO.: 1 or SEQ ID NO.: 2.

In one aspect, the present invention provides a method of screening for a substance that can regulate cell proliferation, comprising contacting cells with a peptide having the same amino acid sequence as the extracellularly secreted BBF2H7 partial peptide, and contacting the cells with a test substance.

In one aspect, the present invention provides a method of screening for a substance that can regulate cell proliferation, comprising contacting a Site-1 protease, a BBF2H7, and a test substance, and detecting the BBF2H7 partial peptide.

In one aspect, the present invention provides a composition for suppressing cell proliferation, comprising a Site-1 protease inhibitor.

In one aspect, the present invention provides a transgenic animal expressing a peptide having the same amino acid sequence as the extracellularly secreted BBF2H7 partial peptide.

In one aspect, the present invention provides a composition for regulating hedgehog signaling, comprising a substance that regulates signaling induced by the extracellularly secreted BBF2H7 partial peptide.

In one aspect, the present invention provides composition for regulating cell cycle, comprising a substance that regulates signaling induced by the extracellularly secreted BBF2H7 partial peptide.

In one aspect, the present invention provides a method of screening for a substance that can inhibit the binding between a peptide having the same amino acid sequence as the extracellularly secreted BBF2H7 partial peptide and a patched1 (Ptch1), comprising contacting the peptide having the same amino acid sequence as the extracellularly secreted BBF2H7 partial peptide, the Ptch1, and a test substance.

BRIEF DESCRIPTION OF THE DRAWINGS

FIG. 7: (A) Amino acid sequences of the BBF2H7 N terminus (upper lines: human, lower lines: mouse). The solid lines indicate the amino acids identical between human and mouse. The dotted lines indicate the amino acids of the same polarity. (B) Amino acid sequences of the BBF2H7 C terminus (upper lines: human (SEQ ID NO.: 1), lower lines: mouse (SEQ ID NO.: 2)). The solid lines indicate the amino acids identical between human and mouse. The dotted lines indicate the amino acids of the same polarity.

FIG. 8: Constructs of full-length BBF2H7, BBF2H7 N terminus, and BBF2H7 C terminus having luciferase protein fused to the C-terminal end. The Black box at the N-terminal end of the BBF2H7 C terminus indicates BiP signal peptide. Luc. indicates luciferase.

DESCRIPTION OF EMBODIMENTS

Figure 1:
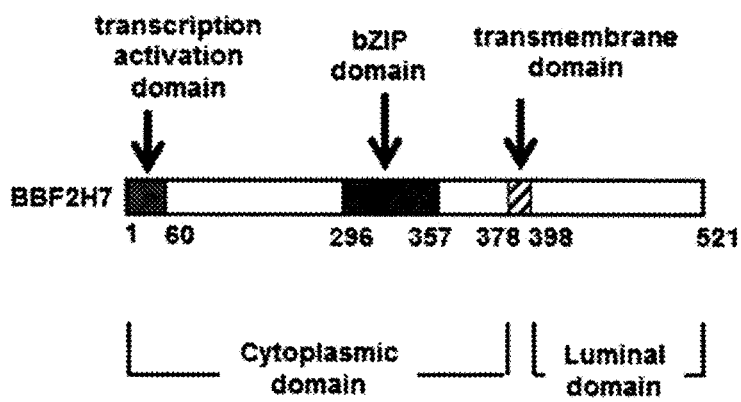
FIG. 1: Structure of mouse BBF2H7.

1. A Composition for Promoting Cell Proliferation Comprising a Substance that Potentiates Signaling Induced by the Extracellularly Secreted BBF2H7 Partial Peptide In one aspect, the present invention provides a composition for promoting cell proliferation comprising a substance that potentiates signaling induced by the extracellularly secreted BBF2H7 partial peptide.

The substance that potentiates signaling induced by the extracellularly secreted BBF2H7 partial peptide may be an agent which activates the intracellular signaling pathway initiated by binding of the extracellularly secreted BBF2H7 partial peptide to the receptor on the cell surface (for example, Ptch1). For example, the substance may be an agent which enhances the expression of Cyclin D, Cyclin E, Cdk2, Cdk4, Gli1 and/or Sec23a gene(s) compared with the expression in the absence of the substance.

1-1. A Composition for Promoting Cell Proliferation Comprising a Peptide having the Same Amino Acid Sequence as the Extracellularly Secreted BBF2H7 Partial Peptide In one embodiment, the substance that potentiates signaling induced by the extracellularly secreted BBF2H7 partial peptide may be a peptide having the same amino acid sequence as the extracellularly secreted BBF2H7 partial peptide. The peptide may be an isolated or synthesized peptide.

BBF2H7 is subjected to regulated intramembrane proteolysis by an enzyme, Site-1 protease, in the cells, to give the C terminus partial peptide that will be secreted extracellularly and the N terminus partial peptide that will not be secreted outside of the cells. The peptide having the same amino acid sequence as the extracellularly secreted BBF2H7 partial peptide may be the extracellularly secreted BBF2H7 C terminus partial peptide or a peptide having the same amino acid sequence to the extracellularly secreted BBF2H7 C terminus partial peptide.

As used herein, the cell may be any cell derived from a mammal, for example, a cell derived from human, rat or mouse. Examples of the cell which secrets the BBF2H7 partial peptide may include a chondrocyte, a fibroblast, a primary cultured chondrocyte, a primary cultured fibroblast, a cell line derived from a chondrocyte, and a cell line derived from a fibroblast.

As used herein, the BBF2H7 is not particularly limited protein and may be a BBF2H7 of any origins such as a human BBF2H7, a mouse BBF2H7, and a rat BBF2H7. Examples of the BBF2H7 used in the present invention include human BBF2H7 and mouse BBF2H7. The amino acid sequence of human BBF2H7 is represented by SEQ ID NO.: 3 and the amino acid sequence of mouse BBF2H7 is represented by SEQ ID NO.: 4.

Examples of the extracellularly secreted BBF2H7 C terminus partial peptide include those of primary cultured mouse chondrocyte (e.g., C57BL/GCR SLC mouse chondrocyte), primary cultured mouse fibroblast (e.g., C57BL/6CR SLC mouse fibroblast), a primary cultured human chondrocyte, and a primary cultured human fibroblast. For example, the extracellularly secreted BBF2H7 C terminus partial peptide may be present in culture medium in which the cells are cultured.

Furthermore, examples of the peptide having the same amino acid sequence as the extracellularly secreted BBF2H7 C terminus partial peptide include a peptide consisting of the amino acid sequence of SEQ ID NO.: 1 (the amino acid sequence of the C terminus partial peptide of human BBF2H7), SEQ ID NO.: 2 (the amino acid sequence of the C terminus partial peptide of mouse BBF2H7), a peptide comprising the amino acid sequence of SEQ ID NO.: 1, and a peptide comprising the amino acid sequence of SEQ ID NO.: 2.

The peptide having the same amino acid sequence as the extracellularly secreted BBF2H7 partial peptide, which can be used for the composition for promoting cell proliferation provided by the present invention, may be a salt or a solvate of the peptide.

In one embodiment, the present invention provides a composition for promoting cell proliferation, comprising an analogue of the peptide having the same amino acid sequence as the extracellularly secreted BBF2H7 partial peptide. Examples of the analogues include an analogue of the extracellularly secreted BBF2H7 C terminus partial peptide and an analogue of the peptide having the same amino acid sequence as the extracellularly secreted BBF2H7 C terminus partial peptide.

Examples of the analogues include a polypeptide consisting of an amino acid sequence having 60, 70, 80, 90 or 95% or more homology to the amino acid sequence of the extracellularly secreted BBF2H7 C terminus partial peptide, and a polypeptide consisting of an amino acid sequence of the extracellularly secreted BBF2H7 C terminus partial peptide in which 1, 2, 3, 4, 5, 6, 7, 8, 9 or 10 amino acid(s) is deleted, substituted or added.

Examples of the analogues include an analogue of the peptide consisting of the amino acid sequence represented by SEQ ID NO.: 1 or 2. The analogue is not particularly limited as long as it can be produced based on the peptide consisting of the amino acid sequence represented by SEQ ID NO.: 1 or 2. Examples of the analogues include a polypeptide consisting of an amino acid sequence having 60, 70, 80, 90 or 95% or more homology to SEQ ID NO.: 1 or 2, and a polypeptide consisting of an amino acid sequence represented by SEQ ID NO.: 1 or 2 in which 1, 2, 3, 4, 5, 6, 7, 8, 9 or 10 amino acid(s) is deleted, substituted or added.

Other examples of the analogues include a tagged BBF2H7 partial peptide.

Therefore, the composition for promoting cell proliferation provided by the present invention may comprise a peptide consisting of the amino acid sequence represented by SEQ ID NO.: 1 or 2 to which a tag is attached. As used herein "tag" means a moiety which is attached to a polypeptide e.g. for purification or detection of the polypeptide. Examples of the tag include histidine (His), glutathione-S-transferase (GST), maltose binding protein (MEP), myc, and FLAG. A polypeptide to which a tag is attached can be obtained, for example, by expressing the polypeptide in a suitable host cell using an expression vector such as pET30a (Novagen, Inc.) (for His-tag) or pGEX (GE Healthcare Bio-Sciences Corp.) (for GST-tag).

Further examples of the analogues include a BBF2H7 partial peptide to which a substituent or a protecting group that is usually used in the field of peptide synthesis, or a substituent or a protecting group that stabilizes the peptide is attached to the N- or C-terminal end.

Therefore, the composition for promoting cell proliferation provided by the present invention may comprise a peptide consisting of the amino acid sequence represented by SEQ ID NO.: 1 or 2 to which a substituent or a protecting group that is usually used in the field of peptide synthesis, or a substituent or a protecting group that stabilizes the peptide is attached at the N- or C-terminal end. Examples of the substituent or the protecting group include, but are not limited to, an amide group, an acetyl group, a benzyloxycarbonyl group (a Cbz group or a Z group), a Boc, and an Fmoc.

In one embodiment, the analogue, e.g., the analogue of the peptide consisting of the amino acid sequence represented by SEQ ID NO.: 1 or SEQ ID NO.: 2, can promote the proliferation of cells, e.g., primary cultured chondrocytes and primary cultured fibroblasts and/or increase expression of cell cycle related genes such as expression of mRNA of Cyclin D, Cyclin E, Cdk2, and Cdk4.

The peptide having the same amino acid sequence as the extracellularly secreted BBF2H7 partial peptide and the analogue thereof, which can be used for the composition for promoting cell proliferation provided by the present invention, can be produced by a conventional technique in biotechnology or biochemistry or a method used in peptide synthesis. For example, the peptide consisting of the amino acid sequence represented by SEQ ID NO.: 1 or 2 can be produced by the following methods:

Expressing the peptide consisting of the amino acid sequence represented by SEQ ID NO.: 1 or 2 in cells such as *Escherichia coli* or other cells using an expression vector to which a nucleotide sequence encoding the amino acid sequence represented by SEQ ID NO.: 1 or 2 is inserted;

Purifying the peptide consisting of the amino acid sequence represented by SEQ ID NO.: 1 or SEQ ID NO.: 2 from a culture medium of a primary culture;

Synthesizing the peptide consisting of the amino acid sequence represented by SEQ ID NO.: 1 or 2 in a solid phase using the Fmoc or Boc method; or Sequentially fusing Boc-amino acids or Z-amino acids by liquid-phase synthesis to produce the peptide consisting of the amino acid sequence represented by SEQ ID NO.: 1 or 2.

The term Fmoc represents a 9-fluorenylmethoxycarbonyl group, Boc represents a t-butoxycarbonyl group, and Z represents a benzyloxycarbonyl group.

The composition for promoting cell proliferation may be used for preparing (producing) cells since promoting cell proliferation increases the amount of cells to be produced.

In one embodiment, the present invention provides use of the peptide having the same amino acid sequence as the extracellularly secreted BBF2H7 C terminus partial peptide, for example, the peptide consisting of the amino acid sequence represented by SEQ ID NO.: 1 or SEQ ID NO.: 2 or an analogue thereof, in the manufacture of a composition for promoting cell proliferation or a composition for preparing (producing) cells.

In one embodiment, the present invention provides a method of promoting cell proliferation or a method of preparing cells, comprising contacting the cells with the peptide having the same amino acid sequence as the extracellularly secreted BBF2H7 C terminus partial peptide, for example, the peptide consisting of the amino acid sequence represented by SEQ ID NO.: 1 or SEQ ID NO.: 2 or an analogue thereof.

The type of the cells whose proliferation is promoted by the present invention is not particularly limited and may be chondrocyte, such as human chondrocyte. A large amount of chondrocytes can be prepared by contacting chondrocytes obtained from a mammal such as human with the composition for promoting cell proliferation provided by the present invention comprising the peptide having the same amino acid sequence as the extracellularly secreted BBF2H7 C terminus partial peptide, for example, the peptide consisting of the amino acid sequence represented by SEQ ID NO.: 1 or SEQ ID NO.: 2 or an analogue thereof.

Therefore, in one embodiment, the present invention provides a composition for promoting proliferation of chondrocyte, comprising a peptide consisting of the amino acid sequence represented by SEQ ID NO.: 1 or SEQ ID NO.: 2 or an analogue thereof.

In addition, in one embodiment, the present invention provides a method of preparing chondrocytes or a method of promoting proliferation of chondrocyte, comprising contacting chondrocytes, such as human chondrocytes, with the composition for promoting cell proliferation provided by the present invention comprising the extracellularly secreted BBF2H7 C terminus partial peptide, for example, the peptide consisting of the amino acid sequence represented by SEQ ID NO.: 1 or SEQ ID NO.: 2 or an analogue thereof.

The method of promoting cell proliferation or the method of preparing cells, such as chondrocytes, may be carried out in vitro, ex vivo or in vivo.

1-2. A Composition for Promoting Cell Proliferation Comprising a Nucleic Acid Molecule In one embodiment, the substance that potentiates signaling induced by the extracellularly secreted BBF2H7 partial peptide may be a nucleic acid molecule encoding the amino acid sequence of the extracellularly secreted BBF2H7 partial peptide. In this embodiment, for example, the nucleic acid molecule encoding the amino acid sequence of the extracellularly secreted BBF2H7 partial peptide may be a nucleic acid molecule encoding the amino acid sequence represented by SEQ ID NO.: 1 or 2.

"Nucleic acid molecule" may be a polynucleotide consisting of two or more nucleotides.

In one embodiment, the present invention provides a composition for promoting cell proliferation, comprising a nucleic acid molecule encoding a peptide consisting of an amino acid sequence having 60, 70, 80, 90 or 95% or more homology to the amino acid sequence represented by SEQ ID NO.: 1 or 2 or a polypeptide consisting of an amino acid sequence represented by SEQ ID NO.: 1 or 2 in which 1, 2, 3, 4, 5, 6, 7, 8, 9 or 10 amino acid(s) is deleted, substituted or added.

Furthermore, in one embodiment, the present invention provides a composition for promoting cell proliferation comprising an analogue of a nucleic acid molecule encoding the amino acid sequence represented by SEQ ID NO.: 1 or 2. Examples of the analogue include a nucleic acid molecule consisting of a nucleotide sequence having 60, 70, 80, 90 or 95% or more homology to a nucleic acid molecule encoding the amino acid sequence represented by SEQ ID NO.: 1 or 2, and a nucleic acid molecule consisting of a nucleotide sequence of a nucleic acid molecule encoding the amino acid sequence represented by SEQ ID NO.: 1 or 2 in which 1, 2, 3, 4, 5, 6, 7, 8, 9 or 10 nucleotide(s) is deleted, substituted or added.

The nucleic acid molecule which can be used for the composition for promoting cell proliferation provided by the present invention may be an isolated nucleic acid molecule.

The nucleic acid molecule which can be used in the aspect of the present invention can be conveniently inserted into a vector and expressed in a host cell. The host cell may be a cell stably expressing the peptide encoded by the vector or the nucleic acid molecule which can be used for the composition for promoting cell proliferation provided by the present invention or a cell transiently expressing it.

Therefore, in one embodiment, the present invention provides a composition, mixture or kit for promoting cell proliferation, comprising a vector comprising a nucleic acid molecule encoding the amino acid sequence represented by SEQ ID NO.: 1 or 2 or a host cell transfected with a nucleic acid molecule encoding the amino acid sequence represented by SEQ ID NO.: 1 or 2.

The composition for promoting cell proliferation provided by the present invention may be a composition for preparing (producing) cells.

In one embodiment, the present invention provide a method of producing cells or a method of promoting cell proliferation, comprising contacting cells, such as human chondrocytes, with a composition or mixture for promoting cell proliferation comprising the nucleic acid molecule encoding the amino acid sequence of the extracellularly secreted BBF2H7 C terminus partial peptide or an analogue thereof, such as the nucleic acid molecule encoding the amino acid sequence represented by SEQ ID NO.: 1 or 2, the vector comprising the nucleic acid molecule, or the host cell comprising the vector.

The cell may be chondrocyte, such as human chondrocyte. A large amount of chondrocytes can be prepared by contacting chondrocytes obtained from a mammal such as human, with the composition or mixture for promoting cell proliferation provided by the present invention comprising the nucleic acid molecule encoding the amino acid sequence of the extracellularly secreted BBF2H7 partial peptide, such as the peptide consisting of the amino acid sequence represented by SEQ ID NO.: 1 or SEQ ID NO.: 2 or an analogue thereof, the vector comprising the nucleic acid molecule or the host cell comprising the vector.

Therefore, in one embodiment, the present invention provides a composition, mixture or kit for promoting chondrocyte proliferation, comprising the nucleic acid molecule encoding the amino acid sequence represented by SEQ ID NO.: 1 or SEQ ID NO.: 2 or an analogue thereof, the vector comprising the nucleic acid molecule or an analogue thereof, or the host cell comprising the vector.

Furthermore, in one embodiment, the present invention provides use of the nucleic acid molecule encoding the amino acid sequence represented by SEQ ID NO.: 1 or SEQ ID NO.: 2 or an analogue thereof, the vector comprising the nucleic acid molecule or an analogue thereof, or the host cell comprising the vector, for manufacturing a composition, mixture or kit for promoting chondrocyte proliferation.

Furthermore, in one embodiment, the present invention provides a method of preparing chondrocytes or a method of promoting chondrocytes proliferation, comprising contacting chondrocytes, such as human chondrocytes, with the composition for promoting cell proliferation provided by the present invention comprising the nucleic acid molecule encoding the amino acid sequence of the extracellularly secreted BBF2H7 C terminus partial peptide or an analogue thereof, such as the peptide consisting of the amino acid sequence represented by SEQ ID NO.: 1 or SEQ ID NO.: 2, the vector comprising the nucleic acid molecule, or the host cell comprising the vector. The composition for promoting cell proliferation or preparing (manufacturing) cells provided by the present invention is suitably formulated using the substance that potentiates signaling induced by the extracellularly secreted BBF2H7 partial peptide, for example, the peptide having the same amino acid sequence as the extracellularly secreted BBF2H7 partial peptide or the nucleic acid molecule encoding it. For example, the composition provided by the present invention can be formulated together with a pharmaceutically acceptable carrier (including an additive). Pharmaceutically acceptable carriers include, but are not limited to, for example, excipients (for example, dextrin, hydroxypropylcellulose, and polyvinylpyrrolidone), disintegrants (for example, carboxymethyl cellulose), lubricants (for example, magnesium stearate), surfactants (for example, sodium lauryl sulfate), solvents (for example, water, saline, and soybean oil) and preservatives (for example, p-hydroxybenzoic acid ester). Those skilled in the art can conveniently determine the method of the formulation, the method of the administration, the subject for the administration, the dosage, and the like of the composition for promoting cell proliferation or the composition for producing (manufacturing) cells provided by the present invention. For example, the composition for promoting cell proliferation or the composition for producing (manufacturing) cells provided by the present invention may be a composition comprising 1 ng to 10 g of the substance that potentiates signaling induced by the extracellularly secreted BBF2H7 partial peptide (for example, the peptide having the same amino acid sequence as the extracellularly secreted BBF2H7 partial peptide or the nucleic acid molecule encoding).

2. A Composition for Suppressing Cell Proliferation Comprising a Substance that Suppresses Signaling Induced by the Extracellularly Secreted BBF2H7 Partial Peptide In one aspect, the present invention provides a composition for suppressing cell proliferation, comprising a substance that suppresses the signaling induced by the extracellularly secreted BBF2H7 partial peptide.

The substance that suppresses the signaling induced by the extracellularly secreted BBF2H7 partial peptide may be a substance that suppresses the intracellular signaling pathway initiated by binding of the peptide to the receptor on the cell surface, such as Ptch1. For example, the substance that suppresses signaling induced by the extracellularly secreted BBF2H7 partial peptide may be a substance that suppresses the transcription of Cyclin D, Cyclin E, Cdk2, Cdk4, Gli1 and/or Sec23a gene(s) initiated by the peptide compared with the transcription in the absence of the substance. Examples of the substance that suppresses signaling induced by the extracellularly secreted BBF2H7 partial peptide include, but are not limited to, a compound, an antibody such as a diabody, a single-chain antibody, a monoclonal antibody, a polyclonal antibody and an antibody fragment, a siRNA, an antisense nucleic acid, a PNA, and a ribozyme.

In one embodiment, the substance that suppresses signaling induced by the extracellularly secreted BBF2H7 partial peptide is an antibody or antibody fragment thereof capable of binding to a peptide having the same amino acid sequence as the extracellularly secreted BBF2H7 partial peptide or an analogue thereof.

In another embodiment, the substance that suppresses signaling induced by the extracellularly secreted BBF2H7 partial peptide is a siRNA that suppresses the expression of human BBF2H7 protein. For example, a siRNA having the same nucleotide sequence as siTrio Full Set Human (CREB3L2, NM_194071) manufactured by COSMO BIO co., ltd (Cat.No.MIR-SHF27A-2213) and a siRNA having a sequence of 80% or more, 85%or more, 90% or more, 95% or more, 98% or more or 99% or more homology to the nucleotide sequence of siTrio Full Set Human may be mentioned. Those skilled in the art can conveniently design such siRNA. For example, they may design a siRNA having a sequence consisting of 19 to 25 nucleotides from the nucleotide sequence that encodes the amino acid sequence of SEQ ID NO.: 1 or SEQ ID NO.: 2.

Any antibodies or antibody fragments capable of binding to the extracellularly secreted BBF2H7 C terminus partial peptide or an analogue thereof can be used for suppressing cell proliferation. The examples include an antibody and antibody fragment capable of binding to the extracellularly secreted BBF2H7 C terminus partial peptide and the full-length BBF2H7 protein, and those capable of binding to the N-terminal end of the extracellularly secreted BBF2H7 C terminus partial peptide but not capable of binding to the full-length BBF2H7 protein.

For example, an antibody or antibody fragment capable of binding to the extracellularly secreted BBF2H7 C terminus partial peptide and the full-length BBF2H7 protein may be generated by a method known in the art using the sequence of the amino acids 431 to 491 in the C terminus of human BBF2H7 as an antigen.

In one embodiment, the present invention provides a composition for suppressing cell proliferation, comprising an antibody or antibody fragment capable of binding to the peptide consisting of the amino acid sequence represented by SEQ ID NO.: 1 or SEQ ID NO.: 2, such as those capable of binding to the peptide and the full-length BBF2H7 protein, those capable of binding to the peptide but not capable of binding to the full-length BBF2H7 protein, or those capable of binding to the N-terminal end of the peptide but not capable of binding to the full-length BBF2H7 protein.

For example, the composition for suppressing cell proliferation provided by the present invention can suppress the unfavorable cell proliferation, and thus, for example, the composition can be used for treating or preventing benign prostatic hypertrophy.

Furthermore, use of the antibody or antibody fragment capable of binding to the extracellularly secreted BBF2H7 C terminus partial peptide or an analogue thereof may suppress proliferation of cancer or tumor cells. Any antibodies or antibody fragments capable of binding to the extracellularly secreted BBF2H7 C terminus partial peptide can be used for suppressing the proliferation of the cancer or tumor cells. Such antibodies or antibody fragments include those capable of binding to the BBF2H7 C terminus partial peptide and the full-length BBF2H7 protein, and those capable of binding to the N-terminal end of the BBF2H7 C terminus partial peptide but not capable of binding to the full-length BBF2H7 protein.

In one embodiment, the present invention provides a composition for treating cancer or tumor or a composition for suppressing proliferation of cancer or tumor cells, comprising an antibody or antibody fragment capable of binding to the peptide consisting of the amino acid sequence represented by SEQ ID NO.: 1 or SEQ ID NO.: 2, such as those capable of binding to the peptide and the full-length BBF2H7 protein, those capable of binding to the peptide but not capable of binding to the full-length BBF2H7 protein, or those capable of binding to the N-terminal of the peptide but not capable of binding to the full-length BBF2H7 protein.

As used herein, the cancer or tumor is not particularly limited and may be a solid tumor or a non-solid tumor. Examples of the cancer or tumor include basal cell carcinoma, neuroectodermal tumors, meningioma, hemangioma, glioblastoma, pancreatic adenocarcinoma, squamous lung carcinoma, small cell lung cancer, non-small cell lung cancer, chondrosarcoma, breast cancer, rhabdomyosarcoma, oesophageal cancer, stomach cancer, biliary tract cancer, renal cancer, thyroid cancer, bone cancer, adrenal cancer, urinary tract cancer, bladder cancer, glioblastoma, and adenocarcinoma, for example, prostate cancer and colorectal cancer such as cecum cancer, colon cancer, and rectal cancer.

As used herein, the antibody includes a polyclonal antibody and a monoclonal antibody.

As used herein, the monoclonal antibodies include a recombinant monoclonal antibody that has been artificially modified for the purpose of reducing xenogeneic antigenicity to a human, such as a chimeric monoclonal antibody, a humanized monoclonal antibody and a human monoclonal antibody.

The antibody fragment is a part of the antibody that can specifically bind to the antigen. Examples of the antibody fragment includes a Fab (fragment of antigen binding), a F(ab')2, a Fab', a single chain antibody (single chain Fv; hereinafter denoted by scFv), a disulfide stabilized antibody (disulfide stabilized Fv; hereinafter denoted by dsFv), a dimerized V region fragment (hereinafter denoted by Diabody), and a peptide containing CDR. See Expert opinion on therapeutic patents, vol. 6, No. 5, p. 441-456, 1996. The antibody and antibody fragment may be produced by a method known in the art. For example, see Antibodies: A Laboratory Manual, Cold Spring Harbor Laboratory Press, 1988, http://www.gene.mie-u.ac.jp/Protocol/Original/Antibody.html, U.S. Pat. Nos. 6,331,415, 5,693,761, 5,225,539, 5,981,175, 5,612,205, 5,814,318, 5,545,806, 7,145,066, 6,492,160, 5,871,907, and 5,733,743. An antibody that specifically recognizes the C- or N-terminal end of the peptide and may be used for the composition for suppressing cell proliferation provided by the present invention may be prepared by a method known in the art. For example, see Shinobu Ohmi, Kunio Tsujimura, Masaki Inagaki, "Experimental Protocol for Anti-Peptide Antibodies", Series of Experimental Protocols, supplementary volume of Cell Technology, Shujunsha. For example, such antibody can be prepared by synthesizing a peptide consisting of 10 amino acid residues from the C- or N-terminal end of the extracellularly secreted BBF2H7 partial peptide, conjugating the peptide to a carrier protein such as BSA with MBS, immunizing a rabbit with the conjugated protein, and isolating the antibody that binds to the C- or N-terminal end of the BBF2H7 partial peptide but does not bind to the full-length BBF2H7 protein by a dot blot method.

Since the antibody or antibody fragment that can be used for the composition for suppressing cell proliferation provided by the present invention can specifically recognize the peptide consisting of the amino acid sequence represented by SEQ ID NO.: 1 or SEQ ID NO.: 2 or the full-length BBF2H7 protein before the enzymatic cleavage in a living body, for example in a human cartilage, the antibody or antibody fragment may be used for detecting the peptide or the protein and further for analyzing e.g. distribution or function thereof.

The antibody that can be used for the composition for suppressing cell proliferation provided by the present invention may have a label attached thereto. Examples of the label include an enzyme, a fluorescent substance, a radioisotope, and biotin.

Examples of the enzyme include alkaline phosphatase, peroxidase, glucose oxidase, tyrosinase, and acid phosphatase.

Examples of the fluorescent substance include fluorescein isothiocyanate (FITC), GFP, and luciferin.

Examples of the radioisotope include $^{125}$I, $^{14}$C, and $^{32}$P.

The composition for suppressing cell proliferation or proliferation of cancer or tumor cells provided by the present invention is appropriately formulated using the substance that suppresses signaling induced by the extracellularly secreted BBF2H7 partial peptide, such as the antibody, antibody fragment or siRNA that can be used for the composition for suppressing cell proliferation provided by the present invention. For example, the composition for suppressing cell proliferation or proliferation of cancer or tumor cells provided by the present invention can be formulated with a pharmaceutically acceptable carrier (including an additive). The pharmaceutically acceptable carriers include, but not limited to, excipients (for example, dextrin, hydroxypropyl cellulose, and polyvinylpyrrolidone), disintegrators (for example, carboxymethyl cellulose), lubricants (for example, magnesium stearate), surfactants (for example, sodium lauryl sulfate), solvents (for example, water, saline, and soybean oil), and preservatives (for example, p-hydroxybenzoic acid ester). For example, the composition for suppressing cell proliferation or proliferation of cancer or tumor cells provided by the present invention may be a composition comprising 1 ng to 10 g of the substance that suppresses signaling induced by the extracellularly secreted BBF2H7 partial peptide, for example, an antibody, antibody fragment or siRNA that can be used for the composition for suppressing cell proliferation provided by the present invention.

The method for administering the composition for suppressing cell proliferation or proliferation of cancer or tumor cells may be selected appropriately by those skilled in the art depending on the age, body weight, and health condition of the subject to be administered. For example, the composition may be administered intravenously.

The subject to be administered includes, but is not limited to, a human.

The amount of the substance that suppresses signaling induced by the extracellularly secreted BBF2H7 partial peptide, for example, an antibody, antibody fragment or siRNA that can be used for the composition for suppressing cell proliferation provided by the present invention, comprised in the composition for suppressing cell proliferation or proliferation of cancer or tumor cells is not particularly limited as long as the composition produces the effect of the present invention. For example, a dosage of 1 ng to 10 mg per 1 kg of body weight may be administered to a human via intravenous infusion. Those skilled in the art also may conveniently determine the method and frequency for the administration.

In one embodiment, the present invention provides use of the antibody or antibody fragment thereof capable of binding to the peptide having the same amino acid sequence as the extracellularly secreted BBF2H7 partial peptide for manufacturing an agent for suppressing cell proliferation, an agent for treating cancer or tumor, or an agent for suppressing proliferation of cancer or tumor cells.

In one embodiment, the present invention provides a method for suppressing cell proliferation, a method for treating cancer or tumor, or a method for suppressing proliferation of cancer or tumor cells, comprising administering the composition for suppressing cell proliferation, the composition for treating cancer or tumor, or the composition for suppressing proliferation of cancer or tumor cells provided by the present invention. The methods may be carried out in vitro, ex vivo or in vivo.

3. A Method of Screening for a Substance that can Regulate Cell Proliferation 1

In one aspect, the present invention provides a method of screening for a substance that can regulate cell proliferation, comprising contacting cells with a peptide having the same amino acid sequence as the extracellularly secreted BBF2H7 partial peptide, and contacting the cells with a test substance. If the substance suppresses proliferation of cancer cells, it can be used as an anticancer agent.

In one embodiment, the present invention provides a method of screening for a substance that suppresses cell proliferation or an anticancer agent, comprising the steps of: contacting cells with a peptide selected from i) to iii) below:
i) a peptide having the same amino acid sequence as the BBF2H7 partial peptide that is secreted extracellularly from a primary cultured chondrocyte;
ii) a peptide consisting of the amino acid sequence represented by SEQ ID NO.: 1 or SEQ ID NO.: 2; and
iii) a peptide consisting of the amino acid sequence having 90% or more homology to the amino acid sequence represented by SEQ ID NO.: 1 or SEQ ID NO.: 2 and having an effect for promoting the cell proliferation, and contacting the cells with a test substance.

Whether the cell proliferation occurred or not can be determined, without limitation, by an assay such as BrdU-incorporation assay or WST-8 assay or by counting the cells.

Accordingly, in one embodiment, the present invention provides a method of screening for a substance that can regulate cell proliferation, comprising contacting cells with a peptide having the same amino acid sequence as the extracellularly secreted C terminus BBF2H7 partial peptide; contacting the cells with a test substance; and carrying out BrdU-incorporation assay or WST-8 assay or counting the cells.

The peptide having the same amino acid sequence as the extracellularly secreted C terminus BBF2H7 partial peptide that is contacted with cells may be a peptide consisting of the amino acid sequence represented by SEQ ID NO.: 1 or SEQ ID NO.: 2 or an analogue thereof. The cells used include, but are not limited to, androgen-sensitive human prostate adenocarcinoma cells (LNCaP), human colon adenocarcinoma cells (LS174T), human glioblastoma (U251MG) cells or mouse fibroblasts (MEF).

The test substance may be a compound, for example, a compound having a molecular weight between 100 and 1000 inclusive or between 100 and 500 inclusive.

As used herein, the substance that can regulate cell proliferation includes a substance that can potentiate cell proliferation and a substance that can suppress cell proliferation.

As a result of the method of screening, if the proliferation of the cells contacted with the extracellularly secreted BBF2H7 C terminus partial peptide and the test substance is more strongly suppressed than the proliferation of the cells contacted with the peptide only, the test substance can be identified as a medicament that suppresses the cell proliferation caused by the BBF2H7 C terminus partial peptide. If the test substance potentiates the cell proliferation, the test substance can be identified as a medicament that potentiates the cell proliferation. The medicament that suppresses the cell proliferation can be used as an anticancer agent.

4. A Method of Screening for a Substance that can Regulate Cell Proliferation 2

BBF2H7 is cleaved by Site-1 protease in a cell. Therefore, regulating activity of the Site-1 protease can regulate production of the BBF2H7 C terminus partial peptide and thus can regulate cell proliferation.

In one aspect, the present invention provides a method of screening for a substance that can regulate cell proliferation, comprising contacting cells with a Site-1 protease, a BBF2H7, and a test substance.

The inhibition of the Site-1 protease activity may suppress proliferation of cancer cells.

Therefore, in one embodiment, the present invention provides a method of screening for a substance that can suppress cell proliferation or an anticancer agent, comprising the steps of:
contacting Site-1 protease, BBF2H7, and a test substance; and
detecting the BBF2H7 partial peptide cleaved by Site-1 protease.

Site-1 protease may be of any origin. For example, Site-1 protease derived from human, mouse, rat or hamster may be used. Those skilled in the art can conveniently prepare Site-1 protease. For example, since the amino acid sequences of human and hamster Site-1 protease (S1P) are described in Sakai, J. et al., Molecular Cell, Vol.2, 505-514, 1998, human and hamster Site-1 protease can be prepared according to the information of the amino acid sequences. Furthermore, human and hamster Site-1 proteases can be prepared according to the information of GenBank accession numbers AF078105 (hamster S1P) and D42053 (human S1P).

BBF2H7 may be a full-length BBF2H7 protein or a partial peptide of BBF2H7 containing the site recognized by Site-1 protease.

The BBF2H7 partial peptide cleaved by Site-1 protease can be detected by any method, for example, HPLC or western blotting.

The test substance may be a compound, for example, a compound having a molecular weight between 100 and 1000 inclusive or between 100 and 500 inclusive.

As a result of the method of screening, if the test substance inhibits the cleavage of BBF2H7 by Site-1 protease, the test substance can be determined to have an effect suppressing cell proliferation or an anticancer effect. On the other hand, when the test substance potentiates the cleavage, the test substance can be determined to have an effect to potentiate cell proliferation.

5. A Composition for Suppressing Cell Proliferation Comprising a Site-1 Protease Inhibitor BBF2H7 is subjected to the regulated intramembrane proteolysis by Site-1 protease, to give the BBF2H7 C terminus partial peptide that has cell proliferation effect. A substance that suppresses the regulated intramembrane proteolysis of BBF2H7 by Site-1 protease inhibits the generation of the BBF2H7 C terminus partial peptide and thus suppresses cell proliferation.

Accordingly, in one aspect, the present invention provides a composition for suppressing cell proliferation, comprising a Site-1 protease inhibitor.

Inhibition of proliferation of cancer cells can be utilized for an anticancer agent. Therefore, the composition for suppressing cell proliferation comprising the Site-1 protease inhibitor may be a composition for treating cancer or tumor, or a composition for suppressing proliferation of cancer or tumor cells. Examples of the cancer or tumor include, but are not limited to, basal cell carcinoma, neuroectodermal tumors, meningioma, hemangioma, glioblastoma, pancreatic adenocarcinoma, squamous lung carcinoma, small-cell lung carcinoma, non-small cell lung carcinoma, chondrosarcoma, breast carcinoma, rhabdomyosarcoma, oesophageal cancer, stomach cancer, biliary tract cancer, renal carcinoma, thyroid carcinoma, bone cancer, adrenal cancer, urinary tract cancer, bladder cancer, glioblastoma, and adenocarcinoma, for example, prostate cancer and colorectal cancer such as cecum cancer, colon cancer, and rectal cancer.

The Site-1 protease inhibitor is not limited as long as it inhibits the regulated intramembrane proteolysis of BBF2H7 by Site-1 protease. For example, the Site-1 protease inhibitor may be a compound, for example, a compound having a molecular weight between 100 and 1000 inclusive or between 100 and 500 inclusive.

The composition for suppressing cell proliferation or for suppressing proliferation of cancer or tumor cells provided by the present invention can be conveniently formulated, for example by blending 1 ng to 10 g of the Site-1 protease inhibitor with a pharmaceutically acceptable carrier (including an additive).

Those skilled in the art can conveniently prepare the composition for suppressing cell proliferation, the composition for treating cancer or tumor, or the composition for suppressing proliferation of cancer or tumor cells.

In one embodiment, the present invention provides use of the Site-1 protease inhibitor for suppressing cell proliferation, treating cancer or tumor, or suppressing proliferation of cancer or tumor cells.

In one embodiment, the present invention provide a method for suppressing cell proliferation, a method for treating cancer or tumor, or a method for suppressing proliferation of cancer or tumor cells, comprising administering the composition for suppressing cell proliferation, the composition for treating cancer or tumor, or the composition for suppressing proliferation of cancer or tumor cells provided by the present invention. The methods may be carried out in vitro, ex vivo or in vivo.

6. A Transgenic Mouse

In one aspect, the present invention provide a transgenic animal expressing a peptide having the same amino acid sequence as the extracellularly secreted BBF2H7 partial peptide, for example, the peptide of SEQ ID NO.: 1 or an analogue thereof, the peptide of SEQ ID NO.: 2. Examples of the transgenic animal include a transgenic mouse.

The transgenic mouse may be prepared by preparing a recombinant DNA fragment having a polynucleotide encoding the extracellularly secreted BBF2H7 partial peptide under control of a suitable promoter, introducing the recombinant DNA fragment to a fertilized egg e.g. by microinjection, transferring a survived fertilized egg to oviduct of a pseudopregnant mouse, and selecting an offspring having the recombinant DNA from the litter. The offspring having the recombinant DNA can be identified, for example, by southern blotting using the genome DNA extracted from the tail of the offspring as a template with a probe having a part of the nucleotide sequence that encodes the extracellularly secreted BBF2H7 partial peptide.

The transgenic animal provided by the present invention may be useful for analyzing the in vivo effect of the extracellularly secreted BBF2H7 partial peptide and the mechanism of the effect. For example, it may be useful for analyzing cell proliferation effect, such as chondrocyte proliferation effect, of the extracellularly secreted BBF2H7 partial peptide, for example, the peptide having the amino acid sequence of SEQ ID NO.: 1 or 2, in vivo.

7. A Composition for Regulating Hedgehog Signaling

In one aspect, the present invention provides a composition for regulating hedgehog signaling comprising a substance that regulates signaling induced by the extracellularly secreted BBF2H7 partial peptide.

The substance that regulates signaling induced by the extracellularly secreted BBF2H7 partial peptide may be a substance that regulates the intracellular signaling pathway initiated by binding of the peptide to a hedgehog receptor, Ptch1, on plasma membrane. For example, the substance that potentiates or suppresses the signaling pathway of the extracellularly secreted BBF2H7 partial peptide may be a substance that potentiates or suppresses transcription of Cyclin D, Cyclin E, Cdk2, Cdk4, Gli1, and/or Sec23a genes initiated by the peptide.

The hedgehogs include sonic hedgehog, Indian hedgehog, desert hedgehog and tiggywinkle hedgehog.

The hedgehog signal is activated by binding of a hedgehog to a cell. Examples include signals activated by Smoothened (SMO), for example, expression of Cyclin D, Cyclin E, Cdk2 or Gli1 gene.

In one embodiment, the substance that suppresses signaling induced by the extracellularly secreted BBF2H7 partial peptide, for example, an antibody or antibody fragment capable of binding to the peptide consisting of the amino acid sequence represented by SEQ ID NO.: 1 or SEQ ID NO.: 2, or a siRNA inhibiting expression of human BBF2H7 protein, suppresses signaling induced by sonic hedgehog, for example, transcription of Cyclin D, Cyclin E, Cdk2 or Gli1 gene.

A compound that suppresses signaling induced by sonic hedgehog is known to be usable for treatment of cancers or tumors. For example, WO2002/030462 discloses examples of tumors for which treatment with a compound that suppresses signaling induced by sonic hedgehog is useful, including tumors related to Gorlin's syndrome (e.g., basal cell carcinoma, medulloblastoma, and meningioma), tumors evidenced in ptc knock-out mice (e.g., hemangioma and rhabdomyosarcoma), tumors resulting from, glui-1 amplification (e.g., glioblastoma and sarcoma), tumors connected with TRC8, a ptc homolog (e.g., renal carcinoma and thyroid carcinoma), Ext-1-related tumors (e.g., bone cancer), Shh-induced tumors (e.g., lung cancer and chondrosarcomas), and other tumors (e.g., breast cancer, urogenital cancer (e.g., kidney, bladder, ureter and prostate cancer), adrenal cancer, gastrointestinal cancer (e.g., stomach and intestine cancer)). Actually, vismodegib, a hedgehog signal inhibitor, has been approved for treating basal cell carcinoma in the United States.

Accordingly, the substance that suppresses signaling induced by the extracellularly secreted BBF2H7 partial peptide and inhibits signaling induced by sonic hedgehog provided by the present invention, for example, an antibody or antibody fragment capable of binding to the peptide consisting of the amino acid sequence represented by SEQ ID NO.: 1 or SEQ ID NO.: 2, or a siRNA inhibiting expression of human BBF2H7 protein, is useful for treating the cancers or tumors listed above. Therefore, the composition for regulating the hedgehog signaling provided by the present invention may be a pharmaceutical composition, for example for treating the cancers or tumors listed above, which can be formulated together with a pharmaceutically acceptable carrier (including an additive). For example, the composition for regulating hedgehog signaling provided by the present invention can be conveniently formulated by blending 1 ng to 10 g of the substance that regulates signaling induced by the extracellularly secreted BBF2H7 partial peptide with a pharmaceutically acceptable carrier (including an additive).

In one embodiment, the present invention provides use of the substance that regulates signaling induced by the extracellularly secreted BBF2H7 partial peptide in the manufacture of a composition for regulating hedgehog signaling.

In one embodiment, the present invention provides a method for regulating hedgehog signaling comprising administering the substance that regulates signaling induced by the extracellularly secreted BBF2H7 partial peptide.

8. A Composition for Regulating Cell Cycle

In one aspect, the present invention provides a composition for regulating cell cycle, comprising a substance that regulates signaling induced by the extracellularly secreted BBF2H7 partial peptide.

The substance that regulates signaling induced by the extracellularly secreted BBF2H7 partial peptide is as described in "7. A composition for regulating hedgehog signaling" above.

In one embodiment, the substance that suppresses signaling induced by the extracellularly secreted BBF2H7 partial peptide, for example, an antibody or antibody fragment capable of binding to the peptide consisting of the amino acid sequence represented by SEQ ID NO.: 1 or SEQ ID NO.: 2, arrests the cell cycle at the $G_0$ or $G_1$ phase and inhibit the progress to the S phase.

Therefore, in one embodiment the present invention provides an agent that inhibits the progress from the $G_1$ phase to the S phase in the cell cycle, comprising the substance that suppresses signaling induced by the extracellularly secreted BBF2H7 partial peptide, for binding to the peptide consisting of the amino acid sequence represented by SEQ ID NO.: 1 or SEQ ID NO.: 2; use of the substance for manufacturing an agent that inhibit the progress from the $G_1$ phase to the S phase in the cell cycle; a method for inhibiting the progress from the $G_1$ phase to the S phase in the cell cycle, comprising administering the substance.

The composition for regulating cell cycle provided by the present invention can be formulated together with a pharmaceutically acceptable carrier (including an additive). For example, the composition for regulating cell cycle provided by the present invention can be conveniently formulated by blending 1 ng to 10 g of the substance that regulates signaling induced by the extracellularly secreted BBF2H7 partial peptide with a pharmaceutically acceptable carrier (including an additive).

9. A Method of Screening for a Substance that can Inhibit Binding Between a Peptide having the Same Amino Acid Sequence as the Extracellularly Secreted BBF2H7 Partial peptide and a Ptch1

In one aspect, the present invention provides a method of screening for a substance that can inhibit binding between a peptide having the same amino acid sequence as the extracellularly secreted BBF2H7 partial peptide and a Ptch1, comprising contacting the peptide, the Ptch1, and a test substance.

The binding between the peptide and the Ptch1 may be detected by any method. For example, the binding may be detected by contacting a cell lysate of androgen-sensitive human prostate adenocarcinoma cells (LNCaP), human colon adenocarcinoma cells (LS174T), human glioblastoma (U251MG) cells, mouse fibroblasts (MEF) or chondrocytes with human BBF2H7 C terminus partial peptide, for example, the peptide consisting of the amino acid sequence represented by SEQ ID NO.: 1 or SEQ ID NO.: 2, immunoprecipitating the peptide with an antibody against the C terminus of BBF2H7, and then subjecting the precipitated complex to western blotting with an anti-Ptch1 antibody.

Therefore, in one embodiment, the present invention provides a method of screening for a substance that can inhibit binding between a peptide having the same amino acid sequence as the extracellularly secreted BBF2H7 partial peptide and a Ptch1, comprising;

the step of contacting the peptide, the Ptch1, and a test substance; and the step of detecting binding between the peptide and the Ptch1 by immunoblotting.

The following examples further illustrate the present invention, but the present invention is not limited to them.

EXAMPLES

Example 1

Establishment of BBF2H7 Knockout Mouse (1) Preparation of a Targeting Vector

A PCR (35 cycles of denature: 94° C. for 1 minute, annealing: 55° C. for 1 minute, and extension: 72° C. for 3 minutes) was performed with the genomic DNA from 129 mouse as a template and primers prepared based on the genomic sequence of the mouse BBF2H7 (ENSMUSG00000038648). DNA fragments of 1.5 kb (short arm) and 6 kb (long arm) around exon 2 of the BBF2H7 gene were isolated. The following primers were used: for the short arm, 5'-GCGGCCGCTTCGACACTTTGTCTGCCACTC-3' (SEQ ID NO.: 5) and 5'-CTCGAGTCACTCCGAGAAGTGCTGCAAGAAGC-3' (SEQ ID NO.: 6); for the long arm, 5'-CAGAGATGCCCTGAGATCAGCTG-3' (SEQ ID NO.: 7) and

5'-GGTACCCTACACCATGCGCCACCAGCCATG-3' (SEQ ID NO.: 8).

The short and long arm DNA fragments were sequenced to confirm no nucleotide substitution was occurred. Subsequently, the DNA fragments were inserted into the NotI-XhoI site (short arm) and the KpnI-KpnI site (long arm) of pPNT1.1 (Cell 1991 Jun. 28, 65 (7): 1153-1163; kindly gifted from Dr. Masaru Okabe (Osaka University, Osaka, Japan)), a vector for targeting, to give the targeting vector.

(2) Transfection

The targeting vector (25 µg/ml) obtained in Example 1 was transfected to cultured undifferentiated mouse ES cells (about $0.8 \times 10^7$) (D3 cell line (Doetschman et al., J Embryol Exp Morphol. 1985, 87:27-45)) by electroporation. The transfected cells were seeded on a culture plate (medium: ESM) and incubated. G418 was added to the medium after 24 hours. G418 and ganciclovir were added to the medium after 48 hours. The cells were incubated for further 7 to 10 days. Colonies resistant to G418 and ganciclovir were obtained. The colonies were isolated and further incubated. DNAs were extracted and analyzed by southern blotting to select ES cells undergoing homologous recombination.

Next, the ES cells undergoing homologous recombination were injected to blastocysts of C57BL/6CR SLC mouse by a conventional method. The blastocysts were transferred to host mice and grown to offspring. As a result, six chimeric mice were obtained. The mice which were assumed to have the transfected ES cells in their germ lines with high probability were selected from the chimeric mice according to the chimeric rate (ratio of brown 129 to black C57BL6). Male mice among the obtained chimeric mice were mated with wild-type female C57B/6 mice to give first generation mice (F1). The F1 mice were analyzed by southern blotting. The southern blotting revealed defects in the BBF2H7 gene. The heterozygous mice for the BBF2H7 gene were selected. The male and female mice having the mutant sequence in one of the diploid chromosomes were selected and mated to give second generation mice (F2).

Genome PCR was carried out with the following primers:
5'-CTGCAGTGOTCAGATGGACAG-3' (SEQ ID NO.: 9),
5'-TGGCTGCGCTGCTGCCCAAGACCCAG-3' (SEQ ID NO.: 10), and
5'-CTTGACGAGTTCTTCTGAGG-3' (SEQ ID NO.: 11) to verify the deletion of the BBF2H7 gene in the knockout mice (−/−).

(3) Characterization of the BBF2H7 Knockout Mouse

The BBF2H7 knockout mice may die due to thoracic hypoplasia immediately after birth. Remarkable shortening of limbs and trunk and skeletal hypoplasia leading to severe thoracic dysgenesis were found in the knockout mice at the fetal stage.

Figure 3:
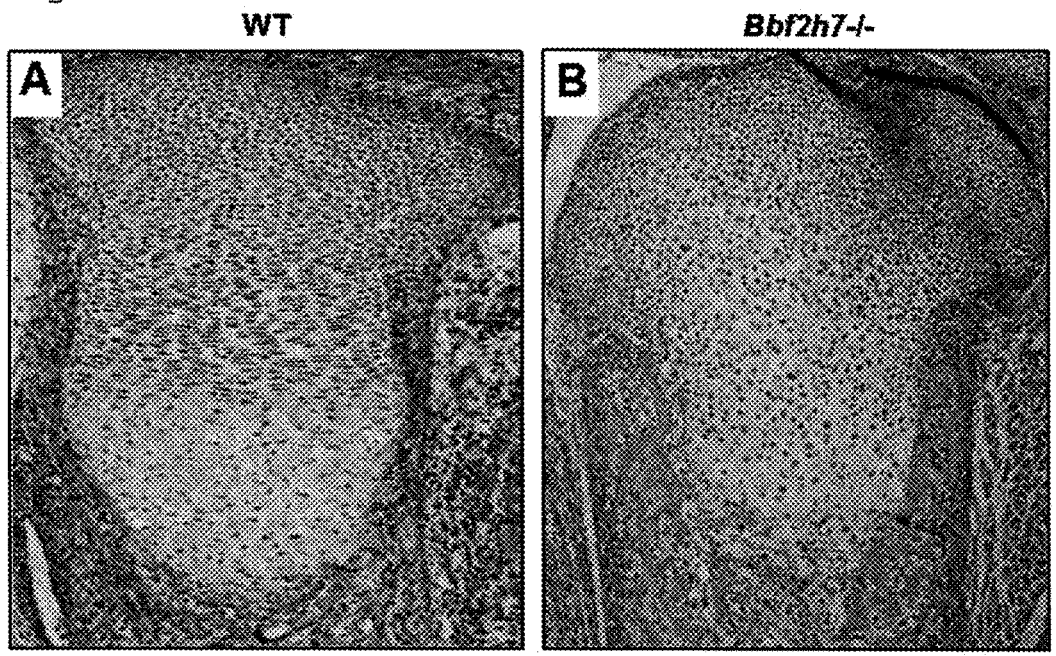
FIG. 3: Hematoxylin and eosin (HE)-stained femur epiphyseal plate of wild-type (WT, (A)) or Bbf2h7-deficient (Bbf2h7 −/−, (B)) mouse at fetal stage (18.5 days). In the Bbf2h7-deficient mouse, the number of the chondrocytes dramatically decreased and the hypochondroplasia occurred.
Figure 4:
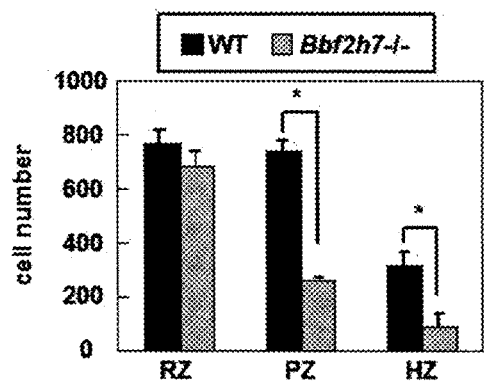
FIG. 4: Number of chondrocytes in zones of resting cartilage, proliferating cartilage, and hypertrophic cartilage. RZ: resting zone, PZ: proliferating zone, HZ: hypertrophic zone (mean±SD, N=3, *P<0.05, unpaired Student's-t-test). In the Bbf2h7-deficient mice the chondrocytes in the zones of proliferating cartilage and hypertrophic cartilage were significantly reduced.

Femur epiphyseal plate of the wild-type (WT) and the Bbf2h7-deficient (Bbf2h7 −/−) mice at the fetal stage (18.5 days) were subjected to hematoxylin-eosin (HE) staining. In the Bbf2h7-deficient mice, the number of the chondrocytes dramatically decreased and the hypochondroplasia was observed (FIG. 3). In the Bbf2h7-deficient mice, the chondrocytes in the zones of proliferating cartilage and hypertrophic cartilage also significantly decreased (FIG. 4).

Example 2

Proliferation of Primary Cultured Chondrocytes from the BBF2H7 Knockout Mouse

Figure 5:
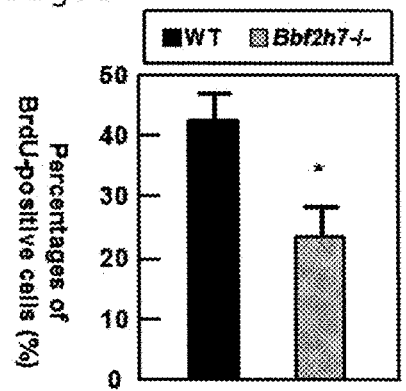
FIG. 5: Result of BrdU-incorporation assay using primary cultured chondrocytes (percentages of BrdU-positive cells (mean ±SD, N=3, *P<0.05, unpaired Student's-t-test)). BrdU was added to the culture media of the primary chondrocytes and the chondrocytes were observed by fluorescence microscope after 24 hours. In the Bbf2h7-deficient cells, the BrdU-incorporation significantly decreased and the cell growth rate was apparently lower.

Primary cultured chondrocytes were derived from the wild-type (WT) mouse (C57BL/6CR SLC mouse) and the Bbf2h7-deficient (Bbf2h7 −/−) mouse (See Saito et al., Nat. Cell Biol. 2009, 11:1197-1204.). Proliferation of the cells was investigated with BrdU-incorporation assay. The assay revealed that BrdU-incorporation was significantly reduced in the Bbf2h7-deficient cells. This result indicates that the cell growth rate was reduced in the Bdf2h7-deficient cells (FIG. 5).

Example 3

Generation of Anti-BBF2H7 Antibody

In order to generate an anti-human BB2H7 C terminus antibody, a mouse was immunized with a partial peptide (IYEEHSPPEESSSPGSAGELGGWDRGSSLLRVSGLES-RPDVDLPHFIISNETSLEKSVLLE (SEQ ID NO.: 12)) as an antigen. Spleen cells were removed from the immunized mouse and fused to myeloma cells. The fused cells were screened for cells producing an antibody which binds to the antigen.

Example 4

Detection of the Secreted BBF2H7 Partial Peptide

Figure 6:
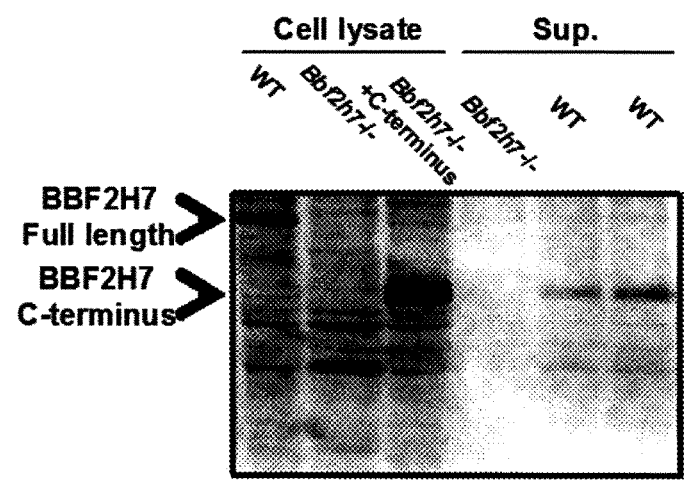
FIG. 6: Western blotting using wild-type (WT) and Bbf2h7-deficient (Bbf2h7−/−) primary cultured chondrocytes. The cell lysates were subjected to western blotting with an anti-BB2H7 C terminus antibody. The culture media (Sup.) of the chondrocytes were subjected to the immunoprecipitation with an anti-BB2H7 C terminus antibody and the obtained fractions were subjected to the western blotting with the anti-BB2H7 C terminus antibody. The band of the BB2H7 C terminus was detected in the culture medium of the wild-type chondrocytes, indicating that the BB2H7 C terminus was extracellularly secreted.

Primary cultured chondrocytes were derived from the wild-type (WT) mouse (C57BL/6CR SLC mouse) and the Bbf2h7-deficient mouse (Bbf2h7 −/−). The cell lysate and culture supernatant (Sup.) were analyzed by western blotting. The cell lysate was subjected to western blotting with the anti-human BB2H7 C terminus antibody. The culture supernatant (Sup.) of the chondrocytes was subjected to the immunoprecipitation with the anti-human BB2H7 C terminus antibody and the fraction obtained by the immunoprecipitation was subjected to western blotting with the anti-human BB2H7 C terminus antibody. The band of the BB2H7 C terminus was detected in the culture supernatant of the wild-type chondrocytes (FIG. 6). The result indicates that the BBF2H7 was subjected to intramembrane proteolysis (RIP, regulated intramembrane proteolysis), the truncated N terminus was translocated into the nucleus to promote transcription of target genes and the C-terminal fragment was extracellularly secreted. The amino acid sequence of the extracellularly secreted BB2H7 C terminus peptide was determined as SEQ ID NO.: 1 (FIG. 7B). The amino acid sequence of the BB2H7 N-terminal peptide was determined as SEQ ID NO.:3 (FIG. 7A).

Figure 9:
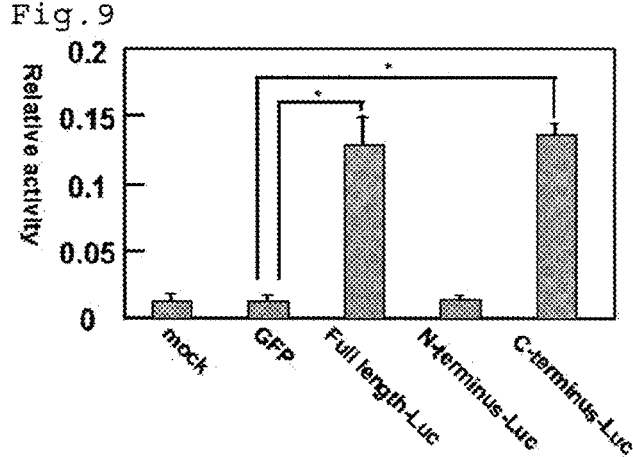
FIG. 9: Luciferase activities in primary cultured chondrocytes expressing constructs of full-length BBF2H7, BBF2H7 N terminus, and BBF2H7 C terminus having luciferase protein fused to the C-terminal end. The three BBF2H7 constructs were transfected to primary cultured chondrocytes, the culture media were collected after 24 hours, and the luciferase activities were measured. The luciferase activities were detected in the culture media of the cells transfected with the full-length BBF2H7 or the BBF2H7 C terminus. The result establishes that the BBF2H7 C terminus was secreted to the culture media.

Subsequently, constructs were prepared by fusing a luciferase protein to each C-terminal end of the full-length BBF2H7, the BBF2H7 N terminus, and the BBF2H7 C terminus (FIG. 8). They were transfected into primary cultured chondrocytes derived from the wild-type mouse (C57BL/6CR SLC mouse). Secretion of the BBF2H7 C terminus peptide into the culture supernatant was investigated. After 24 hours incubation, the culture supernatant was collected and the luciferase activity was measured. The luciferase activity was detected in the culture supernatant of the cells transfected with the full-length BBF2H7 or the BBF2H7 C terminus. The result demonstrated that the BBF2H7 C terminus was secreted into the culture supernatant (FIG. 9).

Example 5

Figure 10:
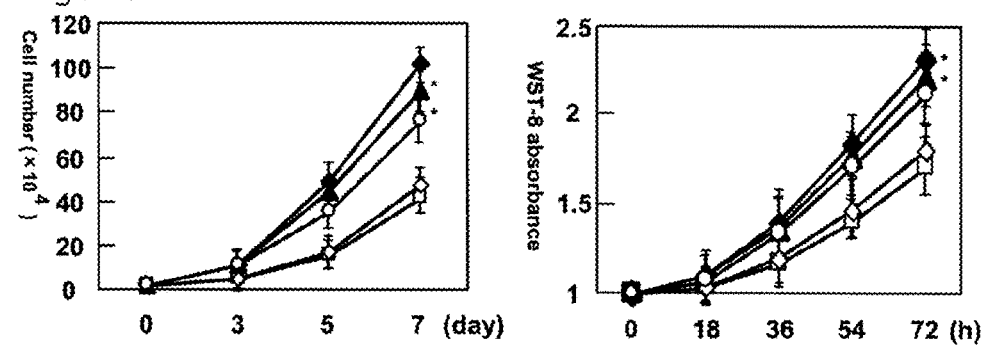
FIG. 10: Cell growth rate of wild-type and Bbf2h7-deficient primary cultured fibroblasts (MEF). (left) Cell number, (right) WST-8 assay. The cell growth rates are shown for ♦: the wild-type cells, □: the Bbf2h7-deficient cells, or the Bbf2h7-deficient cells transfected with ▲: the full-length, ◇: the N terminus or ○: the C terminus of the BBF2H7 (mean ±SD, N=4, *P<0.05, unpaired Student's-t-test). The proliferation of Bbf2h7-deficient MEF was apparently more slowly than the wild-type MEF, but the growth rate of the Bbf2h7-deficient MEF transfected with the full-length or the C terminus of the BBF2H7 was recovered to the level comparable with that of the wild type cells.

Effect of the Secreted Peptide Derived from BBF2H7 on Cell Proliferation of Primary Cultured Fibroblasts Primary cultured fibroblasts (MEF) were derived from the wild-type (WT) mouse (C57BL/6CR SLC mouse) and the Bbf2h7-deficient mouse. Constructs generated by fusing luciferase protein to each C-terminal end of the full-length BBF2H7, the BBF2H7 N terminus and the BBF2H7 C terminus (FIG. 8) were transfected into the Bbf2h7-deficient cells. The cell growth rate was investigated in comparison with the primary cultured fibroblasts (MEF) derived from the wild-type mouse. The cell growth rate was determined by counting the cells (FIG. 10, left) or WST-8 assay (FIG. 10, right). It was revealed that the Bbf2h7-deficient MEF proliferated more slowly than the wild-type MEF and the growth rate of the Bbf2h7-deficient MEF transfected with the full-length BBF2H7 or the BBF2H7 C terminus was recovered to the levels comparable with those in the wild-type cells (FIG. 10).

Figure 11:
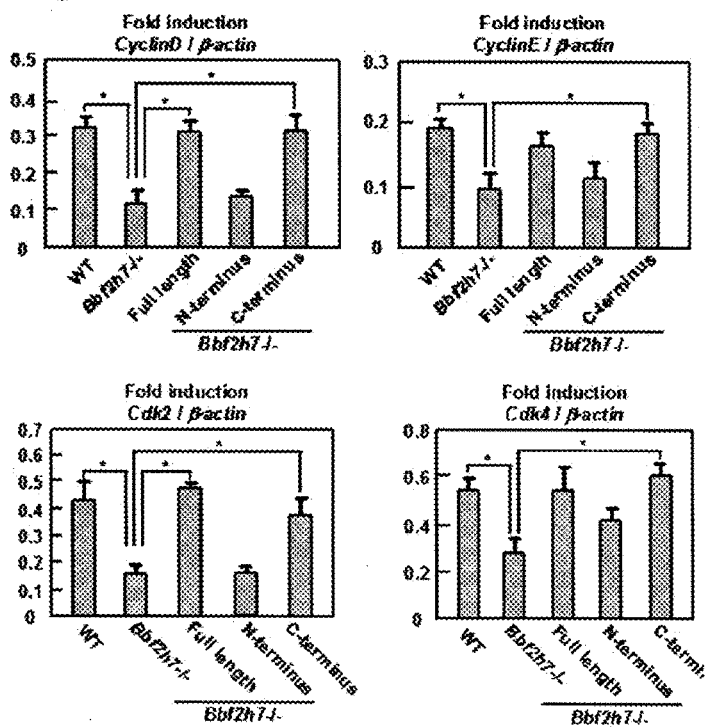
FIG. 11: Real time PCR of various cell cycle-related genes in primary cultured MEF. Full length: the Bbf2h7-deficient cells expressing the full-length BBF2H7, N terminus: the Bbf2h7-deficient cells expressing the BBF2H7 N terminus, C terminus: the Bbf2h7-deficient cells expressing the BBF2H7 C terminus (mean ±SD, N=3, *P<0.05, unpaired Student's-t-test). In the Bbf2h7-deficient MEF (Bbf2h7−/−) the expression levels of the cell cycle-related genes were apparently lower than those in the wild-type MEF (WT), but the expression levels of the genes in the Bbf2h7-deficient MEF transfected with the full-length or the C terminus of the BBF2H7 were recovered to the levels comparable with those in the wild-type cells.

Expression of cell cycle-related genes was measured by real time PCR. In the Bbf2h7-deficient MEF, expression of the cell cycle-related genes was apparently decreased than those in the wild-type MEF. The expression of the genes in the Bbf2h7-deficient MEF transfected with the full-length BBF2H7 or the BBF2H7 C terminus was recovered to the levels comparable with those in the wild-type cells (FIG. 11). For each gene, the following primers were used:

```
Cyclin D
Fwd:
                                    (SEQ ID NO.: 13)
5'-TAGGCCCTCAGCCTCACTC-3'

Rev:
                                    (SEQ ID NO.: 14)
5'-CCACCCCTGGGATAAAGCAC-3'

Cyclin E
Fwd:
                                    (SEQ ID NO.: 15)
5'-CAGAGCAGCGAGCAGGAGC-3'
```

-continued

Rev:
(SEQ ID NO.: 16)
5'-GCAGCTGCTTCCACACCACT-3'

Cdk2
Fwd:
(SEQ ID NO.: 17)
5'-CTGCCATTCTCACCGTGTCC-3'

Rev:
(SEQ ID NO.: 18)
5'-AGCTTGATGGACCCCTCTGC-3'

Cdk4
Fwd:
(SEQ ID NO.: 19)
5'-CGAGCGTAAGATCCCCTGCT-3'

Rev:
(SEQ ID NO.: 20)
5'-GCACCGACACCAATTTCAGC-3'

Example 6

Figure 12:
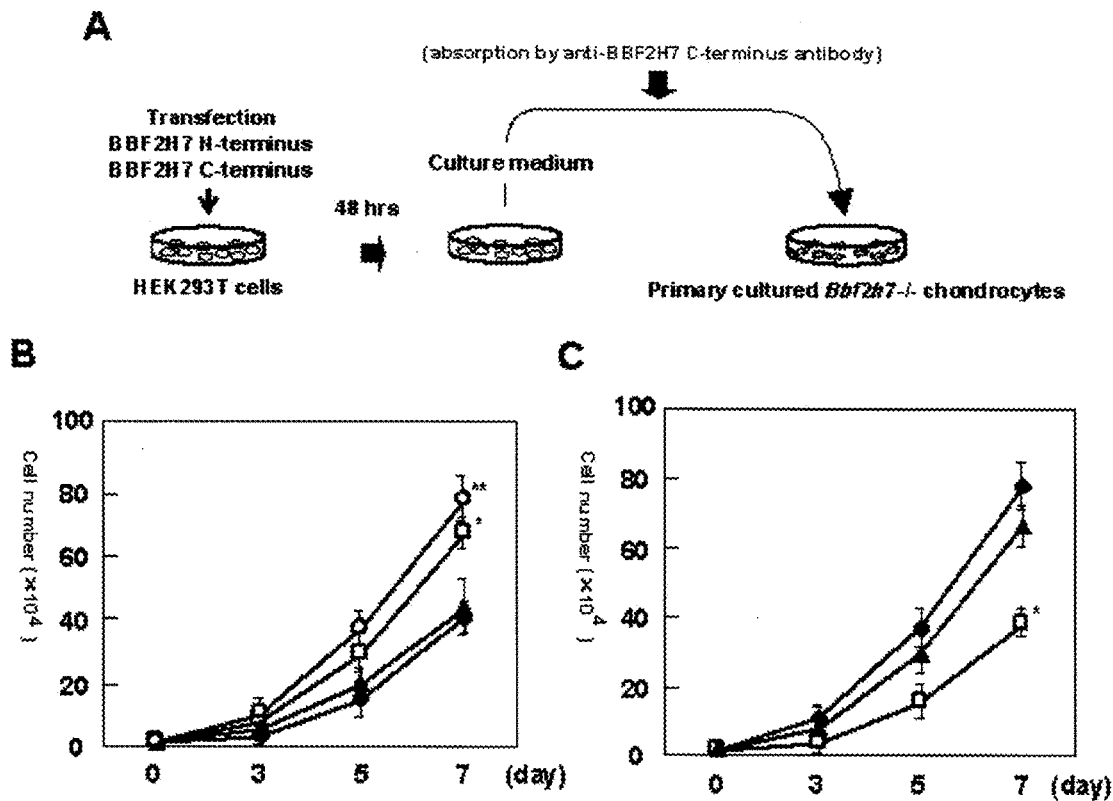
FIG. 12: (A) Experimental system for (B) and (C). For (B), HEK293T cells were transfected with the full-length BBF2H7, the BBF2H7 N terminus or the BBF2H7 C terminus and the culture media were collected after 48 hours. The collected culture media were added to the primary cultured Bbf2h7-deficient chondrocytes and the cells were counted after a fixed period. For (C), HEK293T cells were transfected with the BBF2H7 C terminus and the culture media were collected after 48 hours. The collected culture media were absorbed with an anti-BBF2H7 C terminus antibody and thereby deprived of the secreted BBF2H7 C terminus, and then added to the primary cultured chondrocytes. (B) The lines indicate the growth rates of ♦: the Bbf2h7-deficient chondrocytes, the Bbf2h7-deficient chondrocytes expressing □: the full length, ▲: the N terminus or ○: the C terminus of the BBF2H7 (mean ±SD, N=4, *P<0.05, **P<0.01, unpaired Student's-t-test). The secreted BBF2H7 C terminus functions to recover the growth rate of the Bbf2h7-deficient chondrocytes, the growth rate of which had decreased. (C) The lines indicate the growth rates of ♦: the Bbf2h7-deficient chondrocytes to which the culture medium of the HEK293T cells expressing the BBF2H7 C terminus was added, the Bbf2h7-deficient chondrocytes to which the culture medium of the HEK293T cells expressing the BBF2H7 C terminus was added after absorption by □: an anti-BBF2H7 C terminus antibody or ▲: mouse IgG (mean ±SD, N=3, *P<0.05, unpaired Student's-t-test). Removal of the secreted BBF2H7 C terminus by the BBF2H7 C terminus antibody resulted in the cancellation of the cell proliferative activity.

Effect of the Secreted Peptide Derived from BBF2H7 on Cell Proliferation of Primary Cultured Chondrocytes HEK293T cells were transfected with the full-length BBF2H7, the BBF2H7 N terminus or the BBF2H7 C terminus and the culture supernatants were collected after 48 hours incubation (FIG. 12A). The collected culture supernatant was added to the Bbf2h7-deficient primary cultured chondrocytes (Bbf2h7−/−) and the cells were counted after a fixed period. It was revealed that the BBF2H7 C terminus secreted into the culture medium of cultured HEK293T cells recovered the growth rate of the Bbf2h7-deficient chondrocytes, the growth rate of which had decreased (FIG. 12B). Furthermore, HEK293T cells were transfected with the full-length BBF2H7, the BBF2H7 N terminus or the BBF2H7 C terminus and the culture supernatants were collected after 48 hours. The culture supernatant of the HEK293T cells was deprived of the BBF2H7 C terminus by addition of the anti-human BBF2H7 C terminus antibody and added to the Bbf2h7-deficient primary cultured chondrocytes (Bbf2h7−/−). The removal of the secreted BBF2H7 C terminus by the anti-human BBF2H7 C terminus antibody resulted in the loss of the cell proliferation activity of the BBF2H7 C terminus (FIG. 12C).

Figure 13:
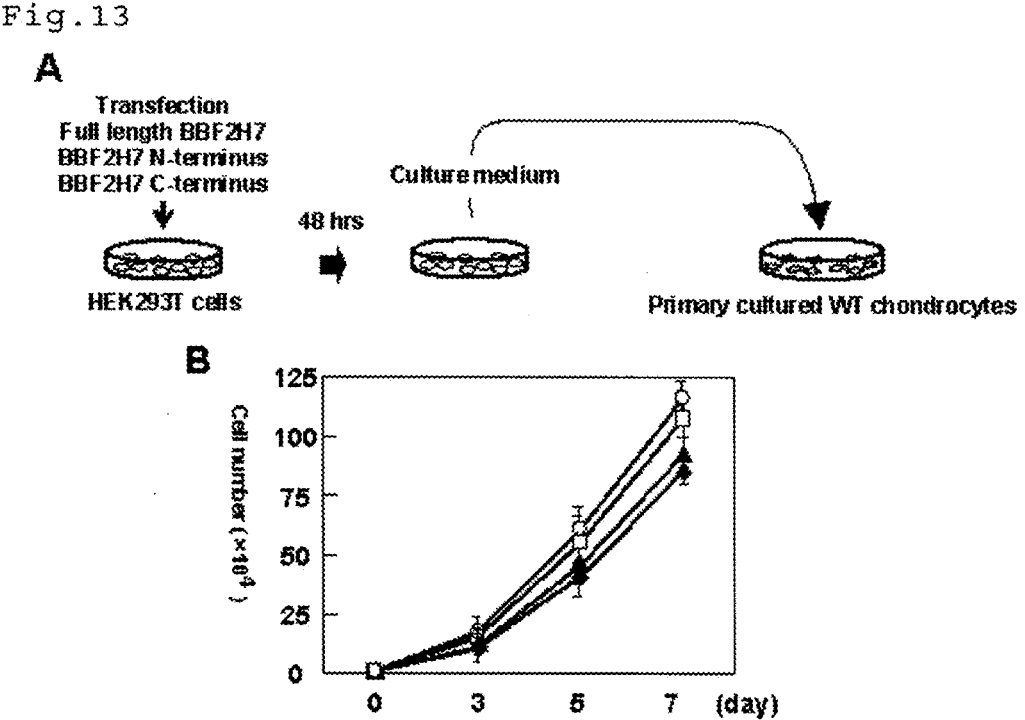
FIG. 13: (A) Experimental system for (B). HEK293T cells were transfected with the full-length, the N terminus or the C terminus of the BBF2H7 and the culture media were collected after 48 hours. The collected culture media were added to primary cultured chondrocytes and the cells were counted after a fixed period. (B) The lines indicate ♦: the wild-type chondrocytes, and the wild-type chondrocytes to which the culture medium of the HEK293T cells expressing □: the full-length, ▲: the N terminus, or ○: the C terminus of the BBF2H7 was added. The BBF2H7 C terminus also has an activity to enhance the proliferation of the wild-type cells.

Moreover, HEK293T cells were transfected with the full-length BBF2H7, the BBF2H7 N terminus or the BBF2H7 C terminus and the culture supernatants were collected after 48 hours incubation. The culture supernatant was added to the primary cultured chondrocytes derived from the wild-type (WT) mouse (C57BL/6CR SLC mouse) (FIG. 13A). Consequently, the BBF2H7 C terminus enhanced the proliferation of the wild-type cells (FIG. 13B).

Example 7

Effect of an Antibody Capable of Binding to the Secreted Peptide Derived from BBF2H7 to Suppress the Proliferation of Cancer Cells HEK293T cells were transfected with the full-length BBF2H7, the BBF2H7 N terminus or the BBF2H7 C terminus and the culture supernatants were collected after 48 hours incubation. Androgen-sensitive human prostate adenocarcinoma cells (LNCaP), human colon adenocarcinoma cells (LS174T) and mouse fibroblasts (MEF) were prepared. For each cell line, the following treatments (i) to (iv) were performed: (i) no treatment; (ii) the culture supernatant of the HEK293T cells mentioned above was added; (iii) the culture supernatant of the HEK293T cells mentioned above supplemented with the anti-human BBF2H7 C terminus antibody was added; or (iv) the culture supernatant of the HEK293T cells mentioned above which were deprived of the BBF2H7 C terminus by the anti-human BBF2H7 C terminus antibody was added.

Figure 14:
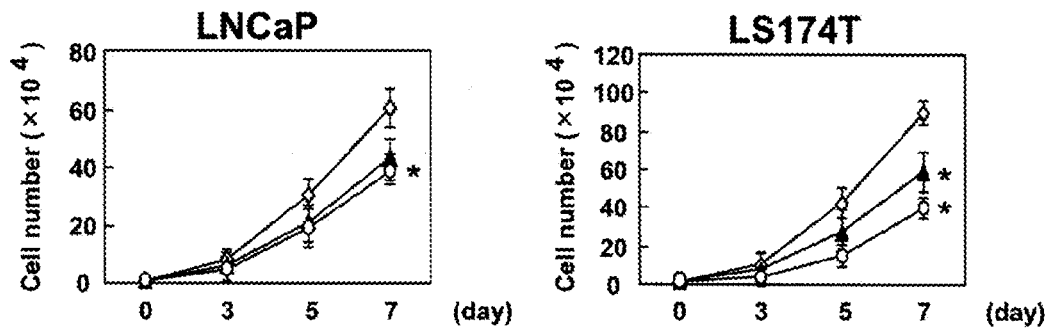
FIG. 14: Growth rates of androgen-sensitive human prostate adenocarcinoma cells (LNCaP), human colon adenocarcinoma cells (LS174T) and mouse fibroblasts (MEF). The lines indicate the growth rates of ◇: the cells with no treatment, ▲: the cells to which an anti-BBF2H7 C terminus antibody was added, ○: the cells to which the culture medium was added after the removal of the secreted BBF2H7 C terminus by absorption with an anti-BBF2H7 C terminus antibody (mean ±SD, N=3: LNCaP, LS174T, N=4: MEF, *P<0.05, unpaired Student's-t-test). The cell growth rate is apparently lower when the anti-BBF2H7 C terminus antibody is added to the cell or the BBF2H7 C terminus is removed from the cells.

As a result, the cell growth rate was suppressed in the cells to which the supernatant supplemented with the anti-human BBF2H7 C terminus antibody was added and the cells to which the supernatant deprived of the BBF2H7 C terminus was added (FIG. 14).

Figure 2:
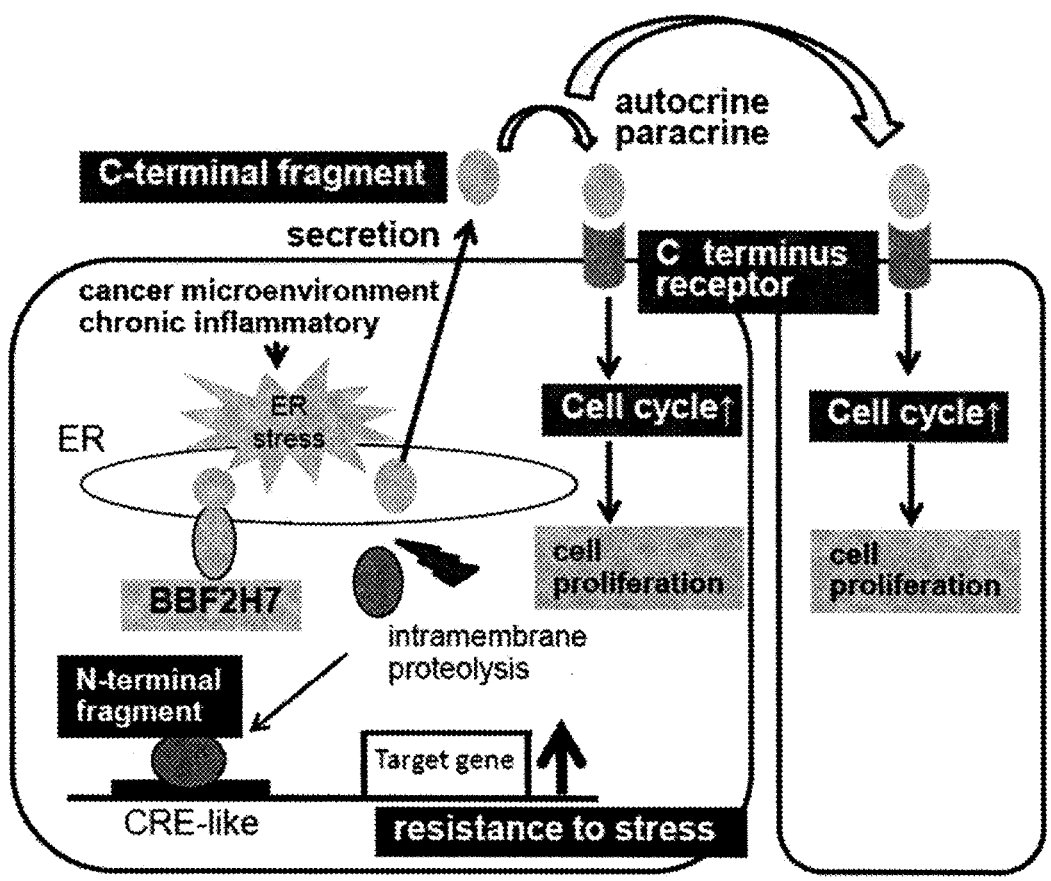
FIG. 2: Function of BBF2H7 C terminus. The BBF2H7 is subjected to intramembrane proteolysis (RIP, regulated intramembrane proteolysis) in response to ER stress caused by cancer microenvironment or chronic inflammatory such as hypoxia and hypoglycemia. The N-terminal fragment induces transcription of target genes for resistance to ER stress. On the other hand, the C-terminal fragment originally located toward ER lumen is extracellularly secreted and bound to BBF2H7 C terminus receptor (Ptch1) expressed on the surface of the cells from which the fragment secreted or the neighboring cells, and thereby promotes cell proliferation.

The experimental results obtained in the examples above indicate that the C-terminal fragment of BBF2H7, which was originally located toward the ER lumen, may be generated by intramembrane proteolysis in response to ER stress caused by cancer microenvironment such as hypoxia and hypoglycemia or by chronic inflammatory, secreted into the extracellular space, and bound to receptors of the BBF2H7 C terminus (Ptch1) expressed on the surface of the cells from which the fragment secreted or the neighboring cells, and thereby promotes the cell proliferation (FIG. 2).

Example 8

Preparation of an Antibody Capable of Binding to the Secreted Peptide Derived from BBF2H7

A recombinant fusion protein of glutathione S-transferase (GST) and the C terminus partial peptide of human BBF2H7 (431-491) (SEQ ID NO.: 12) was expressed in *E. coli* using a vector for generating a GST recombinant protein (GE Healthcare Japan, pGEX4T1, Cat. No.28-9545-49). A mouse was immunized with the obtained GST-fused human BBF2H7431-492 protein. Cells from the immunized mouse were fused with myeloma cells to give 10 clones of hybridoma that produce antibodies capable of specifically binding to human BBF2H7431-492 peptide. Among the 10 clones, clone No.: 6D6 and clone No.: 7E8 were used in the following experiments.

Example 9

Western Blotting of Human Glioblastoma U251MG Cells

Figure 15:
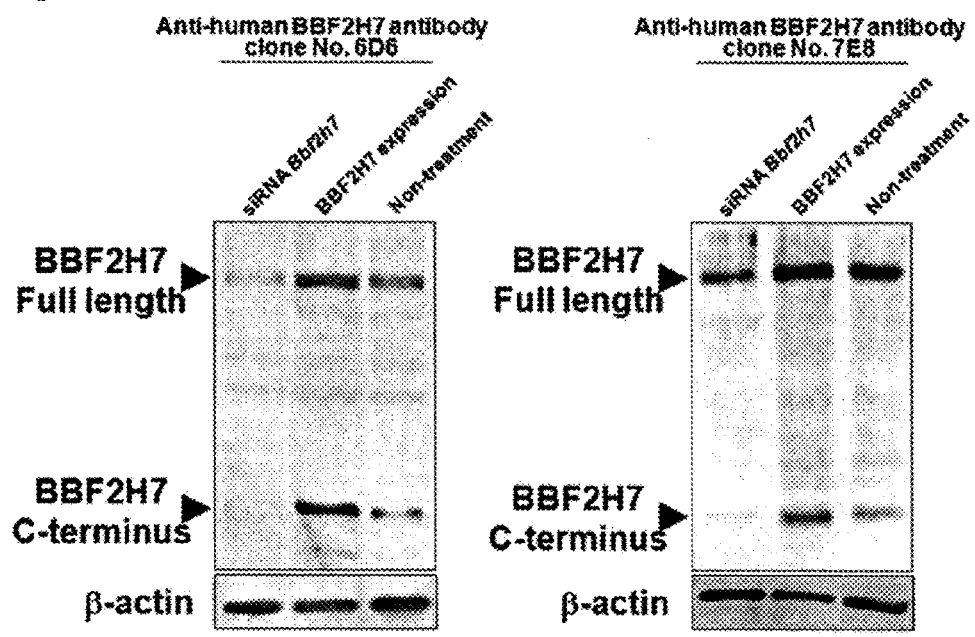
FIG. 15: Western blotting of human glioblastoma U251MG cells. Anti-human BBF2H7 C terminus monoclonal antibodies derived from two hybridomas (6D6, 7E8) were used. The antibodies specifically react with the full-length BBF2H7 and the cleaved C-terminal fragment. siRNA Bbf2h7: the human glioblastoma U251MG cells treated with siRNA Bbf2h7, BBF2H7 expression: the human glioblastoma U251MG cells in which human BBF2H7 is forcedly expressed, Non-treatment: the human glioblastoma U251MG cells without transfection.

In order to confirm that the obtained monoclonal antibodies could bind to the C terminus peptide of human BBF2H7, cell lysates of human glioblastoma U251MG cells and human glioblastoma U251MG cells in which the full-length human BBF2H7 was forcedly expressed were subjected to western blotting with the antibody of clone No.: 6D6 or clone No.: 7E8. Consequently, the two monoclonal antibodies were confirmed to bind to the C terminus peptide of human BBF2H7 (FIG. 15). In addition, it was revealed that the human glioblastoma U251MG cells express a detectable amount of BBF2H7 without the forced expression, and that the expression of the full-length human BBF2H7 was suppressed by treating the human glioblastoma U251MG cells with siRNA (COSMO BIO co., ltd, siTrio Full Set Human (CREB3L2, NM_194071), Cat.No.MIR-SHF27A-2213) and thus the secretion of the C terminus peptide of human BBF2H7 was suppressed (FIG. 15).

Example 10

Figure 16:
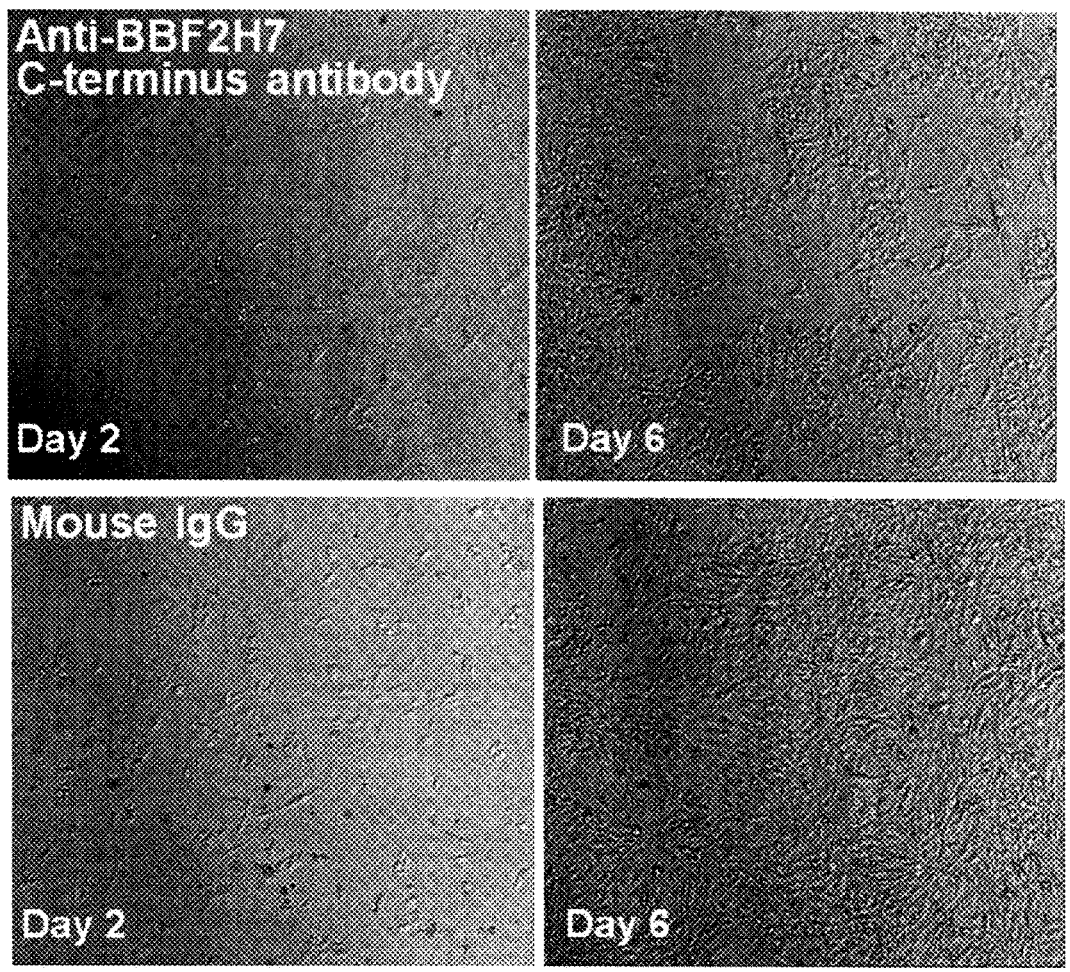
FIG. 16: Effect of anti-human BBF2H7 C terminus monoclonal antibody on proliferation of human glioblastoma U251MG cells. Images were obtained by phase-contrast microscopy. The proliferation of the human glioblastoma U251MG cells was significantly suppressed by the addition of the anti-human BBF2H7 C terminus monoclonal antibody.
Figure 17:
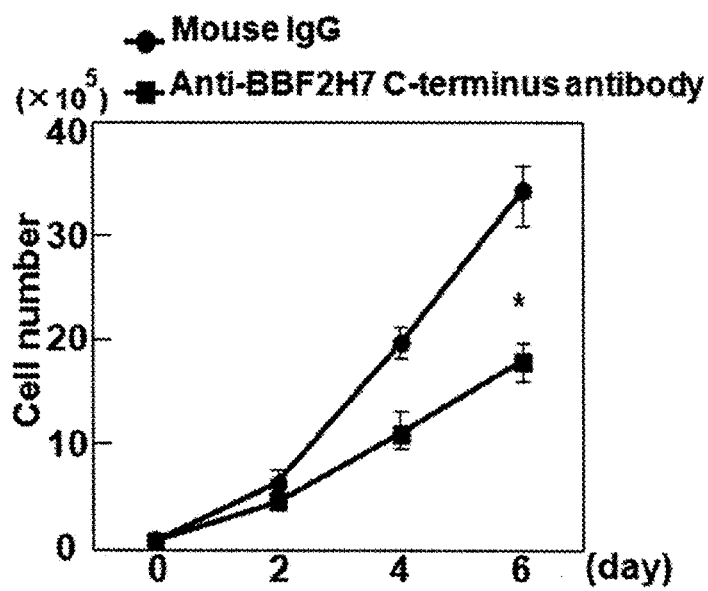
FIG. 17: Effect of anti-human BBF2H7 C terminus monoclonal antibody on the proliferation of human glioblastoma U251MG cells. Time course of cell counts are shown. The proliferation of the human glioblastoma U251MG cells was significantly suppressed by the addition of the anti-human BBF2H7 C terminus monoclonal antibody.
Figure 18:
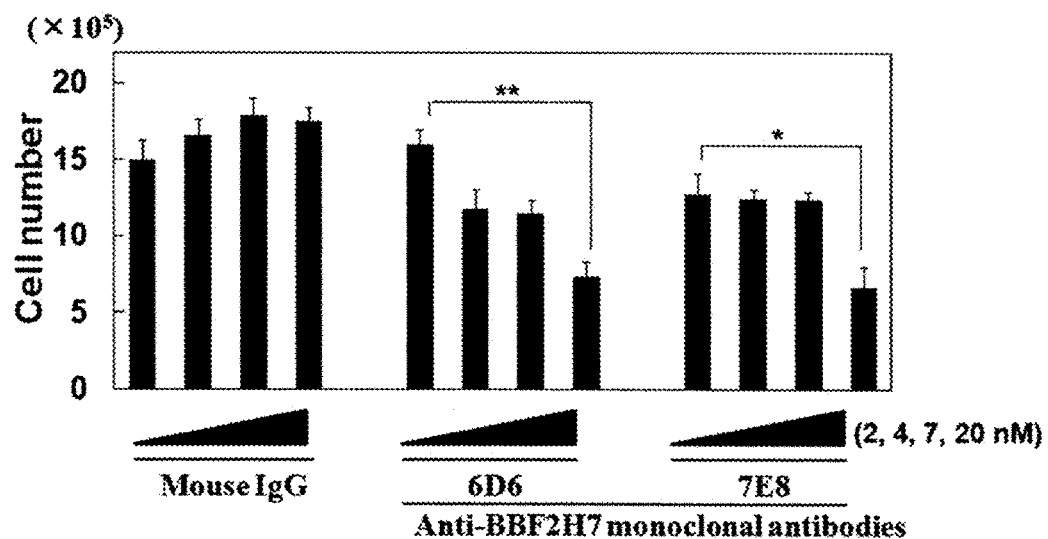
FIG. 18: Effect of anti-human BBF2H7 C terminus monoclonal antibodies to suppress the cell proliferation depending on their concentrations. 6D6 and 7E8 suppressed the proliferation of the human glioblastoma U251MG cells depending on their concentrations.

Effect of the Monoclonal Antibody Capable of Binding to the C Terminus Partial Peptide of Human BBF2H7 to Suppress the Proliferation of Human Glioblastoma U251MG Cells The effect of the monoclonal antibody capable of binding to the C terminus partial peptide of human BBF2H7 on human glioblastoma U251MG cells was studied. Addition of 20 nM of the monoclonal antibody capable of binding to the C terminus partial peptide of human BBF2H7 (clone No.: 6D6) to the human glioblastoma U251MG cells suppressed the cell proliferation (FIG. 16 and FIG. 17). In addition, the monoclonal antibodies capable of binding to the C terminus partial peptide of human BBF2H7 (clone No.:6D6 and clone No.:7E8) suppressed the proliferation of the human glioblastoma U251MG cells in a concentration depending manner (FIG. 18).

Example 11

Figure 19:
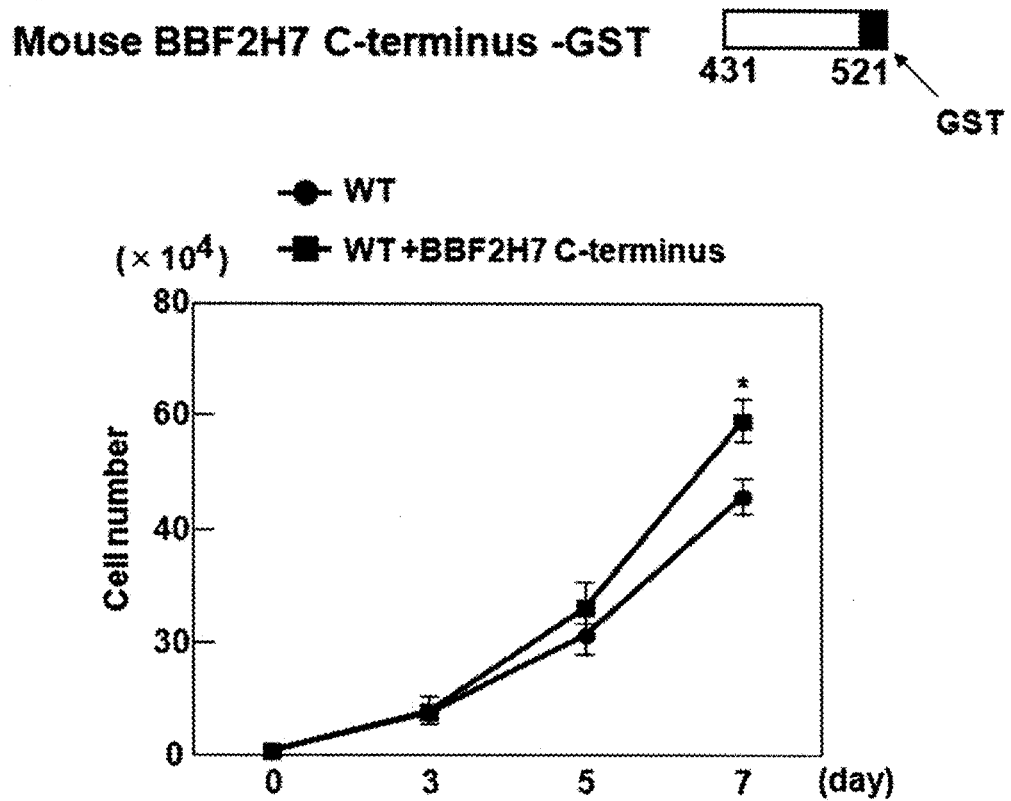
FIG. 19: Effect of BBF2H7 C terminus peptide on proliferation of mouse primary cultured chondrocytes. The mouse BBF2H7 C terminus peptide (431-521) was added to the culture media in a concentration of 75 μg/ml, and then the cells were counted. The count of the cells was higher than that of the cells without the addition of the peptide.

Effect of the C Terminus Partial Peptide of Human BBF2H7 on the Proliferation of Mouse Primary Cultured Chondrocytes A recombinant fusion protein of glutathione S-transferase (GST) and the C terminus partial peptide of human BBF2H7 (431-520) (SEQ ID NO.: 1) was expressed in *E. coli* sing a vector for generating a GST recombinant protein (GE Healthcare Japan, pGEX4T1, Cat. No. 28-9545-49). The obtained GST-fused human BBF2H7431-521 protein was added to the culture media in a concentration of 75 µg/ml, and then the cells were counted. The count of the cells was significantly higher than that of the cells to which no peptide was added (FIG. 19).

Example 12

Binding of the C Terminus Partial Peptide of Human BBF2H7 to Patched1

Figure 20:
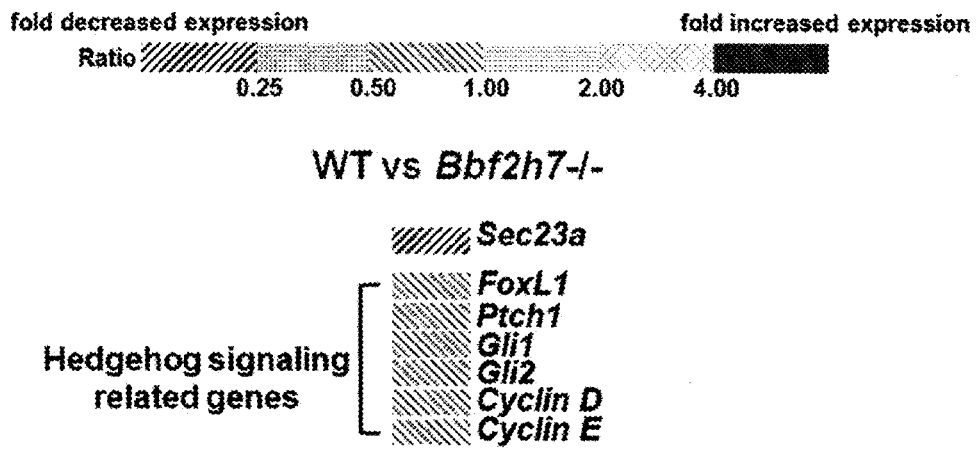
FIG. 20: Result of gene expression profiling in BBF2H7-deficient chondrocytes and wild-type chondrocytes. The expression of every hedgehog signaling related gene in the BBF2H7-deficient chondrocytes was lower than in the wild-type chondrocytes (expression of Sec23a was 0.25-fold or less lower than that in the wild-type cells, expression of FoxL1, Ptch1, Gli1, Gli2, Cyclin D, and Cyclin E was 0.25 to 0.50-fold lower than those in the wild-type cells). Sec23 is a gene identified as a transcription target of the BBF2H7.

Gene expression profiling revealed that the expression of hedgehog signaling related genes in the BBF2H7-deficient chondrocytes was lower than those in the wild-type chondrocytes (FIG. 20). Sec23 is a gene identified as a transcription target of the BBF2H7.

Figure 21:
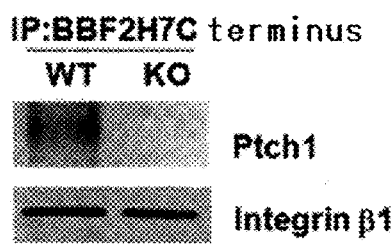
FIG. 21: In order to investigate whether the BBF2H7 binds to Ptch1, a receptor, a cell lysate of the mouse chondrocytes was subjected to the immunoprecipitation with the anti-human BBF2H7 C terminus polyclonal antibody and then the obtained fraction was blotted with a Ptch1 antibody. The result indicates that the peptide was binding to the receptor. Integrin β1 serves as a control.

In order to investigate whether the C terminus partial peptide of human BBF2H7 binds to Patched1 (Ptch1), a hedgehog receptor, cell lysate of the mouse chondrocytes was subjected to the immunoprecipitation with the anti-human BBF2H7 C terminus polyclonal antibody and then the obtained fraction was blotted with anti Ptch1 antibody. The result indicates that the peptide bound to the receptor (FIG. 21, Integrin (β1 serves as a control).

Example 13

Effect of the Antibody Capable of Binding to the C Terminus Partial Peptide of Human BBF2H7 to Suppress Hedgehog Signaling The effect of the antibody capable of binding to the C terminus partial peptide of human BBF2H7 (clone No.: 6D6 and clone No.: 7E8) on the hedgehog signaling was studied. The antibodies were added to the human glioblastoma U251MG cells in a concentration of 20 nM. On the second day, expression levels of the genes were determined by real time PCR. A non-specific mouse IgG antibody (Sigma-Aldrich, MouseIgG murine myeloma clone MOPC-21, Cat. No. M7894) was used as a control. The relative expression amounts of the genes (Cyclin D (CycD), Cyclin E (CycE), CDK2, and GLI1) in the cells treated with clone No.:6D6 and clone No.:7E8 were determined in comparison with the expression amount of β-actin in the cells treated with the non-specific antibody. The same primer sets as Example 5 were used in the real time PCR for CycD, CycE, and CDK2. For GLI1, the following primers were used:

```
SEQ ID NO.: 21:
5'-GGATCGGATAGGTGGTCTTC-3'

SEQ ID NO.: 22:
5'-CCAACTTCTGGCTCTTCCTG-3'
```

Figure 22:
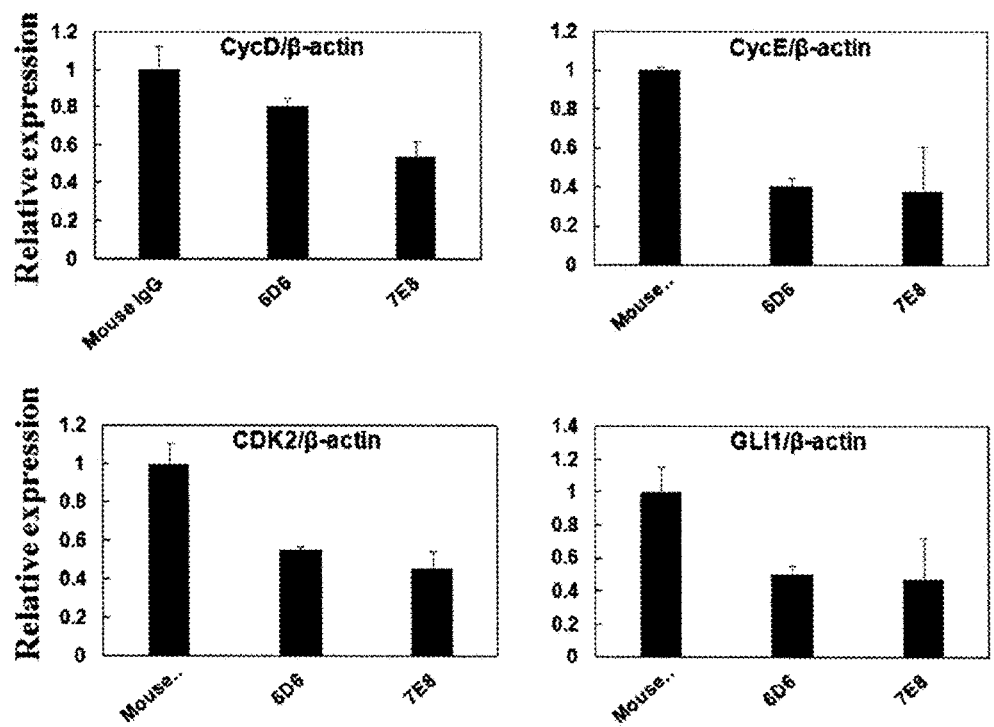
FIG. 22: Effect of anti-human BBF2H7 C terminus monoclonal antibodies on hedgehog signaling. The antibodies were added to human glioblastoma U251MG cells in a concentration of 20 nM. On the second day, the expression levels of the genes (CycD, CycE, CDK2, and GLI1) were determined by real time PCR. The both antibodies (6D6 and 7E8) suppressed the expression of the hedgehog signaling related genes.

The result indicates that the both antibodies suppressed the expression of the hedgehog signaling related genes (FIG. 22).

---

The invention claimed is:

1. A method of increasing cell proliferation, in vitro, comprising culturing a cell in vitro in the presence of a peptide consisting of the amino acid sequence of a Box B-Binding Factor 2 human homologue on chromosome 7 (BBF2H7) C-terminus peptide that is extracellularly secreted, wherein the cell expresses a Patched-1 (Ptch1) BBF2H7 C terminus receptor, and the proliferation of the cell is increased compared to another cell cultured under the same conditions in the absence of the peptide.

2. The method according to claim 1, wherein the amino acid sequence is SEQ ID NO: 1.

3. The method according to claim 1, wherein the peptide is recombinantly produced.

4. The method according to claim 1, wherein the peptide is recombinantly produced with a nucleic acid molecule encoding a peptide consisting of the amino acid sequence represented by SEQ ID NO: 1 or SEQ ID NO: 2.

5. The method according to claim 1, wherein the BBF2H7 C-terminus peptide is from a chondrocyte or a fibroblast.

6. The method according to claim 1, wherein the method increases proliferation of chondrocytes.

7. The method according to claim 1, wherein the method increases proliferation of fibroblasts.

8. The method according to claim 1, wherein the amino acid sequence is SEQ ID NO: 2.

9. The method according to claim 1, wherein the cell is a human cell.

10. The method according to claim 1, wherein
the amino acid sequence is SEQ ID NO: 1 or 2, and
the method increases proliferation of a chondrocyte or a fibroblast.

11. A method of increasing cell proliferation in vitro, comprising
identifying a peptide consisting of the amino acid sequence of a Box B-Binding Factor 2 human homologue on chromosome 7 (BBF2H7) C terminus that is extracellularly secreted, and
culturing a cell in vitro in the presence of the peptide,
wherein the cell expresses a Patched-1 (Ptch1) BBF2H7 C-terminus receptor, and the proliferation of the cell is increased compared to another cell cultured under the same condition in the absence of the peptide.

12. The method according to claim 11, wherein the amino acid sequence is SEQ ID NO: 1.

13. The method according to claim 11, wherein the amino acid sequence is SEQ ID NO: 2.

14. The method according to claim 11, wherein the peptide is recombinantly produced.

15. The method according to claim 11, wherein the peptide is recombinantly produced with a nucleic acid molecule encoding a peptide consisting of the amino acid sequence represented by SEQ ID NO: 1 or SEQ ID NO: 2.

16. The method according to claim 11, wherein the BBF2H7 C-terminus peptide is from a chondrocyte or fibroblast.

17. The method according to claim 11, wherein the cell is a chondrocyte.

18. The method according to claim 11, wherein the cell is a fibroblast.

19. The method according to claim 11, wherein the cell is a human cell.

20. The method according to claim 11, wherein
the amino acid sequence is SEQ ID NO: 1 or 2, and
the method increases proliferation of a chondrocyte or a fibroblast.

* * * * *